US010176412B2

(12) United States Patent
Geissler et al.

(10) Patent No.: US 10,176,412 B2
(45) Date of Patent: Jan. 8, 2019

(54) TRANSPONDERS AND SENSORS FOR IMPLANTABLE MEDICAL DEVICES AND METHODS OF USE THEREOF

(71) Applicant: Establishment Labs S.A., La Garita, Alajuela (CR)

(72) Inventors: Randolph Keith Geissler, Hudson, WI (US); Rudy A. Mazzocchi, Coral Springs, FL (US); Juan José Chacón Quirós, Alajuela (CR)

(73) Assignee: Establishment Labs S.A., La Garita, Alajuela (CR)

( * ) Notice: Subject to any disclaimer, the term of this patent is extended or adjusted under 35 U.S.C. 154(b) by 26 days.

(21) Appl. No.: 15/427,599

(22) Filed: Feb. 8, 2017

(65) Prior Publication Data

US 2017/0228627 A1    Aug. 10, 2017

Related U.S. Application Data

(60) Provisional application No. 62/313,218, filed on Mar. 25, 2016, provisional application No. 62/293,052, filed on Feb. 9, 2016.

(51) Int. Cl.
*A61B 90/98*    (2016.01)
*G06K 19/02*    (2006.01)
(Continued)

(52) U.S. Cl.
CPC .............. *G06K 19/02* (2013.01); *A61B 90/98* (2016.02); *A61F 2/12* (2013.01); *G06K 19/0772* (2013.01); *G06K 19/07758* (2013.01); *G06K 19/07773* (2013.01); *A61F 2002/484* (2013.01); *G06K 19/07* (2013.01)

(58) Field of Classification Search
None
See application file for complete search history.

(56) References Cited

U.S. PATENT DOCUMENTS

| 5,211,129 A | 5/1993 | Taylor |
| 5,373,303 A | 12/1994 | D'Hont |

(Continued)

FOREIGN PATENT DOCUMENTS

| JP | 2010-018482 A | 1/2010 |
| WO | WO 2012/062965 A1 | 5/2012 |

OTHER PUBLICATIONS

International Search Report for PCT/IB2017/000247, dated Aug. 18, 2017 (6 pages).

(Continued)

*Primary Examiner* — Brian Zimmerman
*Assistant Examiner* — Renee Dorsey
(74) *Attorney, Agent, or Firm* — Bookoff McAndrews, PLLC

(57) ABSTRACT

Implantable transponders comprising no ferromagnetic parts for use in medical implants are disclosed herein. Such transponders may assist in preventing interference of transponders with medical imaging technologies. Such transponders may optionally be of a small size, and may assist in collecting and transmitting data and information regarding implanted medical devices. Methods of using such transponders, readers for detecting such transponders, and methods for using such readers are also described.

8 Claims, 11 Drawing Sheets

(51) Int. Cl.
*G06K 19/077* (2006.01)
*A61F 2/12* (2006.01)
G06K 19/07 (2006.01)
A61F 2/48 (2006.01)

(56) References Cited

U.S. PATENT DOCUMENTS

| | | | |
|---|---|---|---|
| 5,482,008 | A | 6/1996 | Stafford et al. |
| 5,833,603 | A | 11/1998 | Kovacs et al. |
| 5,977,431 | A | 11/1999 | Knapp et al. |
| 6,329,958 | B1 | 12/2001 | McLean |
| 6,546,982 | B1 | 4/2003 | Brown et al. |
| 7,508,350 | B2 | 3/2009 | Hein |
| 9,011,333 | B2 | 4/2015 | Geissler et al. |
| 2002/0154065 | A1 | 10/2002 | Mejia |
| 2003/0141963 | A1* | 7/2003 | Furter ............... G06K 19/07743 340/10.51 |
| 2004/0008114 | A1* | 1/2004 | Sawyer ................... G01S 7/003 340/572.1 |
| 2006/0266435 | A1 | 11/2006 | Yang et al. |
| 2007/0159336 | A1* | 7/2007 | Tethrake ................ G06K 19/04 340/572.8 |
| 2008/0106419 | A1* | 5/2008 | Sakama ........... A61B 17/06066 340/572.7 |
| 2009/0270985 | A1 | 10/2009 | Schuessler |
| 2009/0315681 | A1 | 12/2009 | Blair |
| 2010/0004236 | A1 | 1/2010 | Tehim et al. |
| 2011/0226856 | A1 | 9/2011 | Meilland et al. |
| 2011/0257491 | A1* | 10/2011 | Robertson ............ A61B 5/0031 600/302 |
| 2011/0259965 | A1 | 10/2011 | Mejia |
| 2011/0297306 | A1 | 12/2011 | Yang |
| 2013/0131800 | A1 | 5/2013 | Schuessler |
| 2013/0199027 | A1 | 8/2013 | Singh et al. |
| 2014/0078013 | A1* | 3/2014 | Mejia ..................... H01Q 1/002 343/788 |
| 2014/0081398 | A1 | 3/2014 | Mejia et al. |
| 2016/0128798 | A1* | 5/2016 | Bovet .............. G06K 19/07771 206/459.5 |
| 2016/0211924 | A1* | 7/2016 | Deng .................... H04B 11/00 |
| 2017/0256850 | A1 | 9/2017 | Mejia |

OTHER PUBLICATIONS

International Search Report for PCT/US2013/059988, dated Dec. 5, 2013 (3 pages).
International Search Report for PCT/US2013/059964, dated Jan. 10, 2014 (2 pages).
European Search Report for European Application No. 13836381.7, dated Apr. 26, 2016 (2 pages).

* cited by examiner

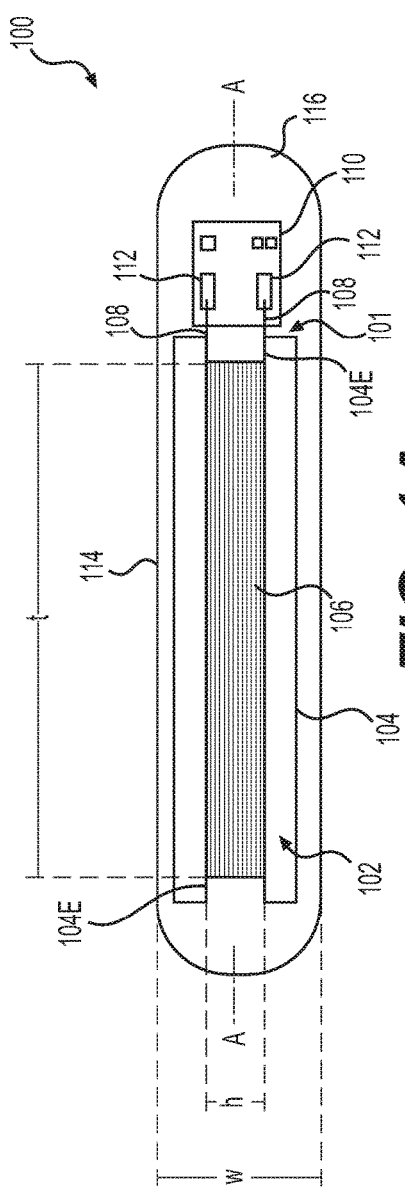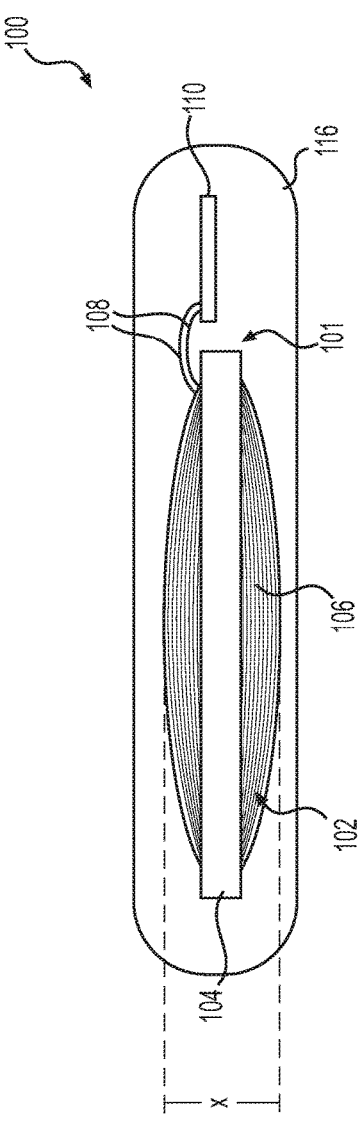
FIG. 1A
FIG. 1B

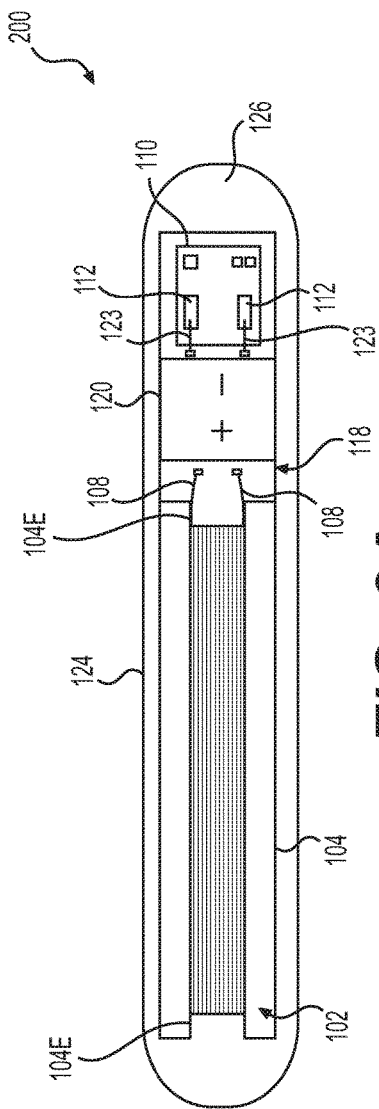
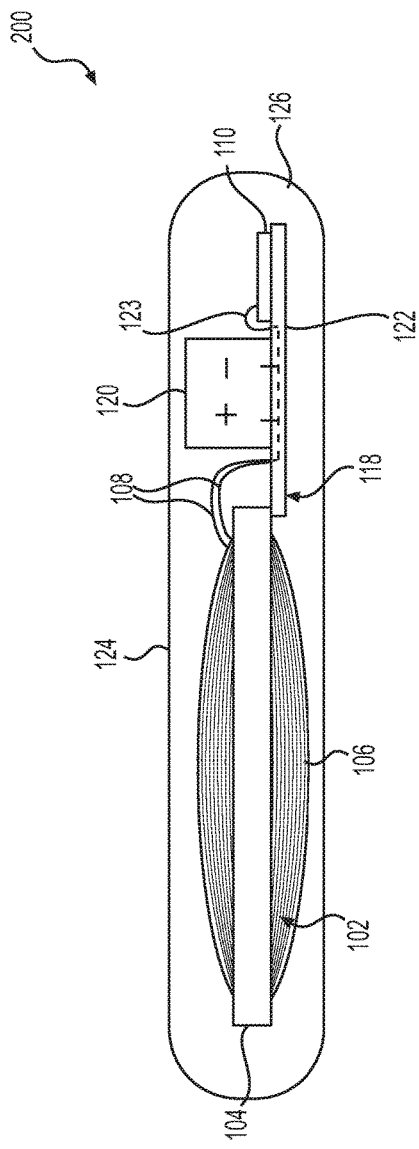
FIG. 2A
FIG. 2B

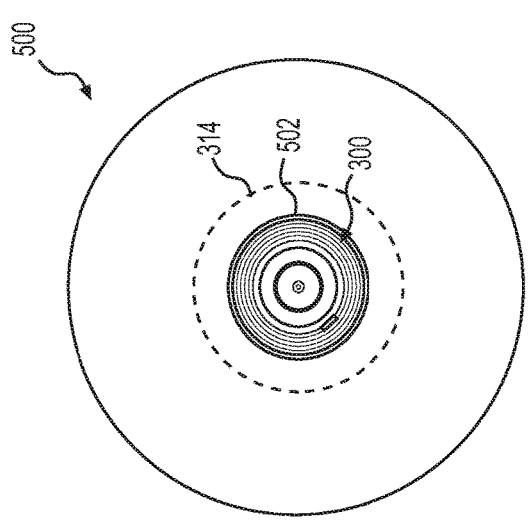
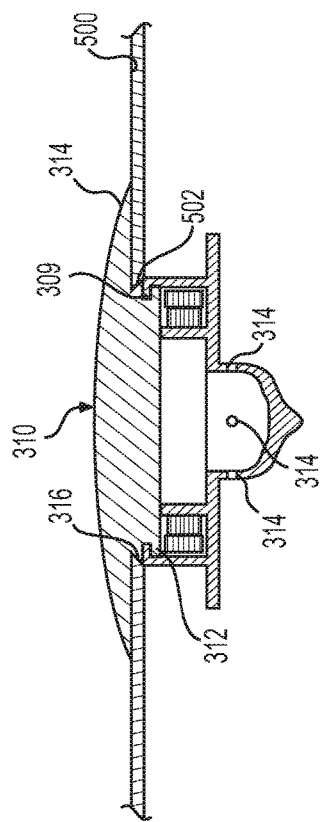
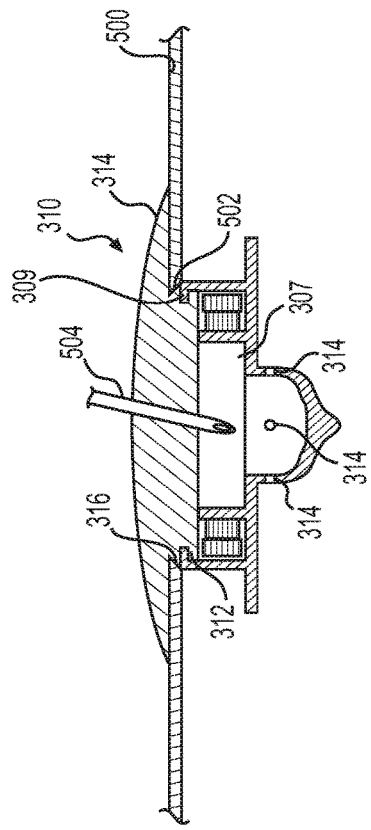

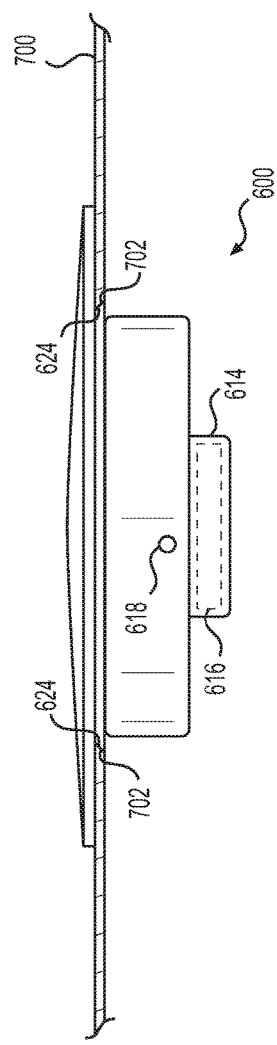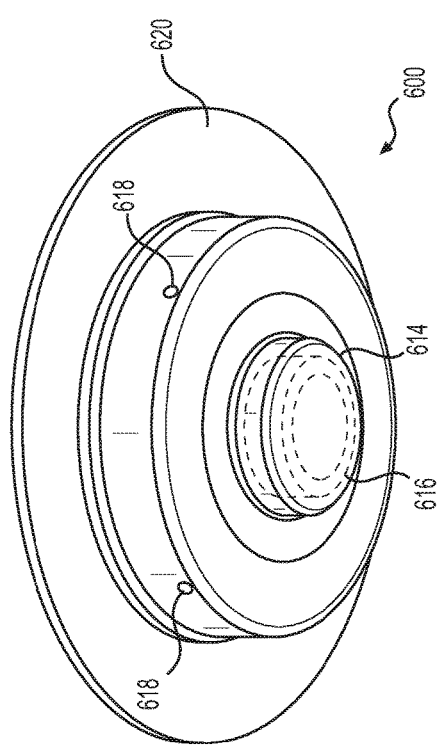
FIG. 7A
FIG. 7B

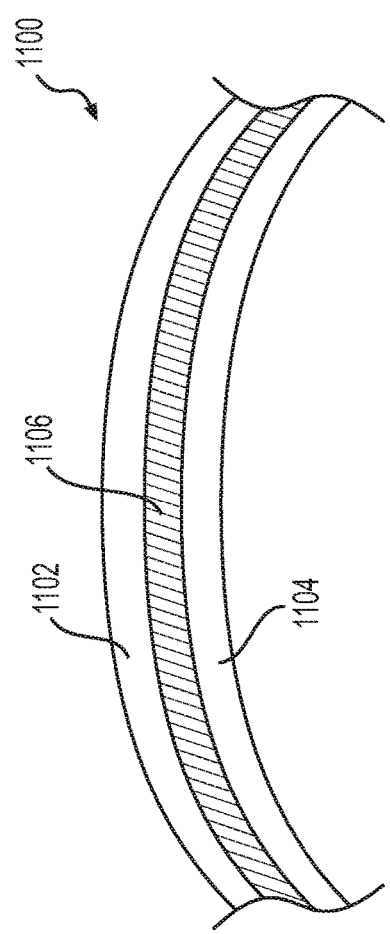

TRANSPONDERS AND SENSORS FOR IMPLANTABLE MEDICAL DEVICES AND METHODS OF USE THEREOF

CROSS-REFERENCE TO RELATED APPLICATIONS

This disclosure claims priority to U.S. Provisional Application No. 62/313,218, filed on Mar. 25, 2016, and U.S. Provisional Application No. 62/293,052, filed on Feb. 9, 2016, each of which is incorporated by reference herein in its entirety.

FIELD OF DISCLOSURE

The present disclosure relates generally to transponder and sensor systems for use with implantable medical devices, implants incorporating such systems, and methods of use thereof.

BACKGROUND

Implantable medical devices may be implanted into patients for a variety of reasons, including, for example, to improve the clinical condition of a patient, to replace natural patient tissue, or for aesthetic purposes. In many cases, implantable medical devices are implanted in patients having severe, complex, or chronic medical conditions. For example, breast implants may be used in reconstructive surgeries following mastectomies, e.g., after a cancer diagnosis, surgical removal of breast tissue, radiation therapy, and/or chemotherapy.

There are many situations in which implantable medical devices and the tissue in which they are implanted may need to be examined, monitored, identified, or further altered after implantation, either by invasive or noninvasive means. For example, after implantation of a medical device, follow-up may be required to monitor healing, check for clinical improvement, and/or screen for development or reappearance of other medical conditions in the vicinity of the medical device (e.g., the reappearance of cancerous tissue in a patient in remission). As a further example, it may be advantageous to be able to identify characteristics of an implanted device, such as the device's model, size, shape, lot number, or other characteristics, without performing an invasive procedure to visually inspect the device. As yet another example, some implantable medical devices may require adjustment after implantation. For example, tissue expanders, such as those which may be used in patients undergoing breast augmentation or reconstruction surgery, may be designed to be incrementally expanded over time.

Various technologies have been developed in order to improve the safety and efficacy of breast implants and other implantable medical devices, in part to address some of the above concerns. Among these technologies is the use and integration of transponders, such as radio-frequency identification (RFID) transponders, in implantable medical devices. Such transponders may be used, for example, to transmit information from within a patient's body, such as information about a location of the device in the patient's body, or a location of a portion of the device in the patient's body. As another example, such transponders may be used to transmit information about an implanted device itself by way of, e.g., a serial number encoded on a chip in each transponder. Information about the implanted device may be useful for, e.g., determining whether the device is subject to any recalls, determining the materials in the device, and planning further surgeries. Information about implantable medical devices may also be useful prior to implantation, such as to track the devices from manufacturing, through storage, sale, transport, delivery to medical centers, and implantation in patients. Microtransponders, such as transponders which have a length of less than three centimeters and a width of less than a centimeter, may provide the added advantage of being small enough for inclusion within implantable medical devices without substantially affecting, e.g., the size, shape, feel, or function of those devices.

However, safety of implantable medical devices, and compatibility of implantable medical devices with continued patient care, are also a concern. Transponders within implanted medical devices may interfere with the use of certain diagnostic, imaging, or other medical techniques on patients having implants with such transponders. For example, in patients requiring monitoring, examination, and/or screening after implantation of a medical device, it may be necessary for the device to be compatible with the use of various scanning, imaging, and diagnostic techniques, such as magnetic resonance imaging (MM), radiography, ultrasound, tomography, etc. Transponders known in the art may, for example, include ferromagnetic parts, which may interfere with, e.g., an MM performed on a patient having such a transponder in his or her body. Such interference may include, for example, the production of an artifact (e.g., a small imaging void) in imaging results taken of a patient. In such cases, the presence of the artifact in the imaging result may be associated with an increased risk of missing a diagnosis of a patient's condition. For example, a medical professional may miss a diagnosis of recurring cancer due to the artifact obscuring a portion of an MRI showing cancerous cells in the patient. As another example, a rupture in an implant, which may normally be visible on MRI results, may be obscured by an artifact in the results caused by a transponder. As a result, MRI might not be a recommended imaging technique for such a patient, or MRI may need to be combined with another imaging technique such as ultrasound, which may incur additional time and expenses on the part of both the patient and medical professionals. As a further example, transponders of a small size may be difficult for an external reader to read after implants containing those transponders have been implanted in a patient. Alternately, a medical professional may prefer not to use an implant which includes a transponder that would produce unwanted artifacts in imaging results, and/or which may be difficult to read.

SUMMARY

The present disclosure includes implantable transponders comprising features that may provide for increased safety, compatibility with medical imaging technology and other procedures, and decreased necessity for invasive procedures. While portions of this disclosure refer to breast implants and tissue expanders, the devices and methods disclosed herein may be used with other implantable medical devices, such as, e.g., other implants used in cosmetic and/or reconstruction procedures (e.g., gastric implants, gluteal implants, calf implants, testicular implants, penile implants), pacemaker components (e.g., pacemaker covers) and other electro-stimulator implants, drug delivery ports, catheters, orthopedic implants, vascular and non-vascular stents, and other devices.

The present disclosure includes, for example, a transponder comprising an electromagnetic coil and a core comprising a non-ferromagnetic material, wherein a length of the transponder is between about 5 mm and about 30 mm, and a width of the transponder measures between about 2 mm and about 5 mm. The transponder may further comprise a capsule enclosing the electromagnetic coil and the core. The transponder may also comprise an integrated circuit chip coupled to the coil. A diameter of the coil may be greater than the width of the transponder. The core may comprise a core width and a core length, wherein the core length is greater than the core width, and wherein the coil is wrapped around the core such that the core length defines an inner diameter of the coil. The transponder may define a longitudinal axis along its length, and the electromagnetic coil may include a wire wound along the direction of the longitudinal axis. The transponder may also comprise an integrated circuit chip coupled to each of two ends of the coil, a glass capsule enclosing the electromagnetic coil, the integrated circuit chip, and an inner space between the glass capsule and the electromagnetic coil and integrated circuit chip, and an adhesive material filling at least 30% of the inner space.

The present disclosure also includes, for example, a transponder comprising a coil comprised of a wire, wherein a length of the transponder measures between about 5 mm and about 30 mm, a width of the transponder measures between about 2 mm and about 5 mm and is less than the length of the transponder, the transponder does not include a ferromagnetic material, and the wire is wound around the length of the transponder. The transponder may further comprise an integrated circuit chip coupled to the coil. The transponder may further comprise a capsule enclosing the coil and the integrated circuit chip coupled to the coil. A diameter of the coil may be smaller than the length of the transponder and greater than the width of the transponder. The transponder may be configured to send and/or receive information within a range of from about 1 inch to about 5 feet. The wire may be an enameled copper wire. The transponder may be wound around a core comprising biocompatible poly-ether-ether-ketone (PEEK). The transponder may be cylindrical.

The present disclosure also includes, for example, a transponder comprising an electromagnetic coil, an RFID chip, and a capsule enclosing the electromagnetic coil and the RFID chip, wherein a length of the capsule is between about 5 mm and about 30 mm, a diameter of the capsule perpendicular to the length is between about 2 mm and about 5 mm, and the transponder does not include a ferromagnetic material. The transponder may define a longitudinal axis along its length, and the electromagnetic coil may include a wire wound along the direction of the longitudinal axis. The electromagnetic coil may be wound around a core comprising biocompatible poly-ether-ether-ketone (PEEK). The core may comprise two notched ends, and the electromagnetic coil may include a wire wound around the core such that turns of the wire sit in each of the two notched ends. A longest diameter of the electromagnetic coil may be longer than a height of the coil.

The present disclosure also includes, for example, an integrated port assembly, comprising a chamber configured to receive a fluid, a wire coil, the coil sharing a central axis with the chamber, and a port dome covering an opening into the chamber. The wire coil may be an electromagnetic coil. The wire coil may have two ends, wherein each end is coupled to an integrated circuit chip. The port dome may seal the chamber of the integrated port assembly. The port dome may also be self-sealing. The integrated port assembly may further comprise a wall defining a side of the chamber, the wall comprising at least one fluid exit hole. The integrated port assembly of claim may further comprise a wire coil chamber housing the wire coil.

The present disclosure also includes, for example, an integrated port assembly, comprising a chamber configured to receive a fluid, the chamber having a fluid entry hole and a plurality of fluid exit holes, a wire coil surrounding the chamber, and a patch covering the fluid entry hole of the chamber. The chamber may further include a needle puncture-resistant surface opposite the fluid entry hole. The fluid entry hole may define a plane, and each of the plurality of fluid exit holes may define a plane perpendicular to the plane defined by the fluid entry hole. The wire coil may have two ends, wherein each end is coupled to an integrated circuit chip, and wherein the wire coil has an outer diameter of between about 10 mm and about 50 mm. The integrated port assembly may further comprise at least four fluid exit holes. The integrated port assembly may further comprise a coil chamber housing the wire coil, wherein the coil chamber is impermeable to fluids. The integrated port assembly may be configured to be used with a breast tissue expander. The patch of the integrated port assembly may be configured to attach to the exterior of the breast tissue expander. The patch may also be self-sealing.

The present disclosure further includes, for example, an integrated port assembly comprising a casing defining a fluid injection chamber configured to receive a fluid via a fluid entry hole, a wire coil in a coil chamber, the coil chamber being isolated from the fluid injection chamber, the coil having a central axis aligned with a center of the fluid injection chamber, and a port dome covering the fluid entry hole of the fluid injection chamber. The fluid injection chamber may comprise a plurality of fluid exit holes. The integrated port assembly may further comprise an integrated circuit chip in the coil chamber, wherein two ends of the wire coil are coupled to the integrated circuit chip. The coil may have an inner diameter of between about 15 mm and about 35 mm.

The present disclosure further includes a method for broadcasting a transponder-specific signal, the method comprising: broadcasting, in a range of a transponder, radio frequency signals across a sweep of frequencies; evaluating a signal strength of each of received return signals from the transponder; determining a frequency of a broadcasted radio frequency signal corresponding to the received return signal having the greatest signal strength; and broadcasting a radio frequency signal at the determined frequency. The method may further comprise receiving, at a plurality of antennas, the return signals having a plurality of signal strengths. The method may further comprise: receiving a plurality of return signals having a plurality of signal strengths; amplifying received return signals having signal strengths below a threshold; and converting the amplified signals to digital values. The step of evaluating the signal strength of the received return signals may comprise converting the received return signals to digital values. The sweep of frequencies may include frequencies within a range of from about 120 kHz to about 140 kHz. The range of the transponder may be about 5 feet.

The present disclosure further includes a system for broadcasting a transponder-specific signal, the system comprising a microcontroller and at least one antenna, the microcontroller being programmed with instructions for performing steps of a method, the method comprising: broadcasting, in the range of a transponder, radio frequency signals across a sweep of frequencies; evaluating a signal strength of each of received return signals from the transponder; determining a frequency of a broadcasted radio frequency signal corresponding to received return signal having the greatest signal strength; and broadcasting a radio frequency signal at the determined frequency. The at least one antenna may comprise at least two antennas, and the method may further comprise receiving, at the at least two antennas, a plurality of return signals having a plurality of signal strengths. The system may further comprise a logarithmic amplifier and an analog-to-digital converter, and the method may further comprise: receiving, at the plurality of antennas, a plurality of return signals having a plurality of signal strengths; amplifying, using the logarithmic amplifier, received return signals having signal strengths below a threshold; and converting received and amplified signals to digital values using the analog-to-digital converter. The step of evaluating the strength of the received return signals may comprise converting the received return signals to digital values. The sweep of frequencies may include frequencies within a range of from about 120 kHz to about 140 kHz. The range of the transponder may be about 5 feet. The system may further comprise a clock generator and a signal driver for performing the step of broadcasting radio frequency signals across a sweep of frequencies. The step of evaluating the strength of received return signals from the transponder may comprise instructing at least one analog-to-digital converter to convert received return signals into digital values, and comparing the digital values to one another.

The present disclosure further includes, for example, a method for broadcasting a transponder-specific signal, the method comprising: broadcasting, in a range of a transponder, radio frequency signals across a sweep of frequencies using a signal driver and an antenna; receiving, using the antenna, return signals from the transponder; amplifying, using a logarithmic amplifier, return signals from the transponder which are below a threshold; converting, using an analog-to-digital converter, received return signals and amplified signals into digital values; evaluating, using a microcontroller, the digital values to determine the strongest return signal or signals; determining a frequency of a broadcasted radio frequency signal corresponding to the strongest received return signal or signals from the transponder; and broadcasting, using the signal driver and antenna, a radio frequency signal at the determined frequency. The method may further comprise receiving, at a pickup antenna, return signals from the transponder which are below the threshold. The step of broadcasting, in the range of a transponder, radio frequency signals across a sweep of frequencies may further comprise using a clock generator to determine a timing of the sweep of frequencies. The method may further comprise displaying, on an LED display, the determined frequency. The sweep of frequencies may include frequencies within a range of from about 120 kHz to about 140 kHz. The range of the transponder may be less than five feet.

BRIEF DESCRIPTION OF THE DRAWINGS

The accompanying drawings, which are incorporated in and constitute a part of this specification, illustrate various examples and together with the description, serve to explain the principles of the present disclosure. Any features of an embodiment or example described herein (e.g., device, method, etc.) may be combined with any other embodiment or example, and are encompassed by the present disclosure.

FIGS. 1A and 1B show an exemplary transponder, according to some aspects of the present disclosure.

FIGS. 2A and 2B show another exemplary transponder, according to some aspects of the present disclosure.

FIGS. 5A-5C shows an exemplary integrated port valve assembly, according to some aspects of the present disclosure.

FIGS. 7A and 7B show further views of the exemplary integrated port valve assembly shown in FIG. 6, according to some aspects of the present disclosure.

FIG. 11 shows an exemplary implant shell according to some aspects of the present disclosure.

DETAILED DESCRIPTION

Figure 3B:
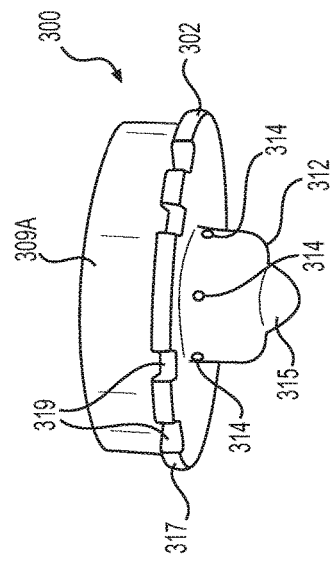
FIGS. 3A-3C show an exemplary valve assembly, according to some aspects of the present disclosure.

Aspects of the present disclosure are described in greater detail below. The terms and definitions as used and clarified herein are intended to represent the meaning within the present disclosure. The terms and definitions provided herein control, if in conflict with terms and/or definitions incorporated by reference.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value.

The present disclosure generally relates to medical implants, features of medical implants, transponders and sensors for use with such implants, and methods of using such transponders, sensors, and implants. Various aspects of the present disclosure may be used with and/or include one or more features disclosed in U.S. Provisional Application No. 62/313,218, entitled "Sensors for Implantable Medical Devices and Methods of Use Thereof," filed on Mar. 25, 2016; U.S. Provisional Application No. 62/293,052, entitled "Identification System Including Transponder With Non-Magnetic Core," filed on Feb. 9, 2016; U.S. Provisional Application No. 62/318,402, entitled "Medical Imaging Systems, Devices, and Methods," filed on Apr. 5, 2016; U.S. Provisional Application No. 62/323,160, entitled "Minimally-Invasive Apparatus for the Implantation of Medical Devices and Methods of Use Thereof," filed on Apr. 15, 2016; U.S. Provisional Application No. 62/334,667, entitled "Implant Surface Technologies and Elements of Formation," filed on May 11, 2016; U.S. Application Publication No. 2015/0282926; U.S. Application Publication No. 2014/0081398; and/or U.S. Application Publication No. 2014/0078013.

Aspects of the present disclosure may be useful for collecting and/or analyzing data relevant to a patient, including, e.g., physiological data and information about medical devices that may be implanted in the patient. Devices, systems, and methods disclosed herein may also be useful for locating and/or altering medical devices that may be implanted in the patient, including, e.g., adjusting the size, shape, and/or position of medical devices that may be implanted in the patient. Such implantable medical devices may include, but are not limited to, breast implants, gluteal implants, tissue expanders, and other medical devices in the field of aesthetic or reconstructive surgery, as well as other types of medical devices configured for temporary or permanent implantation inside a patient. Devices, systems, and methods disclosed herein may also be useful for overcoming challenges presented in the prior art, such as, e.g., artifacts produced by implanted transponders in patient imaging results, and difficulty in reading transponders having weak signals.

As discussed herein, transponders, such as microtransponders, that are designed to avoid the creation of imaging artifacts (referred to herein as "low-artifact transponders"), may be incorporated into implantable medical devices to monitor the status of the medical devices over time and/or to obtain certain types of patient data based on, among other things, the location of the transponders when implanted inside the patient's body.

As also discussed herein, valve assemblies having locator coils, such as integrated port assemblies designed for use in implants requiring periodic addition of fluids such as, e.g., tissue expanders, may be incorporated into implantable medical devices to assist in noninvasive location of valve assemblies after the medical devices have been implanted inside the patient's body.

Readers configured to read multiple types of reading transponders and locator coils, and methods of finding and broadcasting optimal signals for reading such transponders and/or locator coils, are also disclosed herein.

Various data analyses techniques, systems, and methods for use in combination with the transponders, coils, and readers disclosed herein are also disclosed.

Transponders

The present disclosure includes low artifact transponders/chips that may comprise materials and/or design configurations to minimize interference that may be observed from magnetic resonance imaging (MRI), fluoroscopic (X-ray) imaging, and/or ultrasound imaging. As previously noted, MRI, X-ray and ultrasound tests are frequently used for mammography and related tissue analysis to diagnose early signs of breast cancer, and to assess other unrelated heart and lung diseases. The transponders herein may be incorporated into breast implants and tissue expanders to decrease the amount of interference with diagnostic imaging.

Such transponders may be small in size, in order to avoid affecting the size and shape of implants in which they are included. Such transponders may also include materials that are alternatives to ferromagnetic materials, which can cause an imaging artifact under magnetic resonance imaging. For example, the transponders herein may comprise non-ferromagnetic materials, such as poly-ether-ether-ketone (PEEK), other plastics, ceramic, or silica (e.g., glass). Such transponders may also include configurations, such as antenna coil configurations, which are designed to compensate for a lower antenna signal strength associated with small antenna coils having no ferromagnetic core.

FIGS. 1A and 1B depict, in schematic form, a top-down view (FIG. 1A) and a side view (FIG. 1B) of an exemplary transponder 100, which may embody one or more aspects of the present disclosure. Transponder 100 may include an assembly 101, which may include an antenna 102 and a chip 110. Antenna 102 may include an antenna core 104 and an antenna coil 106. Antenna 102 may be connected to a chip 110 via antenna coil ends 108, which may be attached to bond pads 112 of chip 110. A capsule 114 may enclose assembly 101 and an inner space 116, which may surround assembly 101.

Transponder 100 may be configured, for example, to allow for collection and/or transmission of data continuously, intermittently/periodically, and/or on-demand (e.g., prompted by a user). Transponder 100 may have any of a variety of shapes and sizes suitable for inclusion in an implant. For example, transponder 100 may have a size and shape suitable for inclusion in a breast implant, such as a silicone-filled breast implant suitable for implantation in a patient during breast augmentation or reconstruction surgery. In some embodiments, for example, transponder 100 may have a size and shape suitable for inclusion in an implant without substantially altering the size, shape, or weight of the implant. In some embodiments, transponder 100 may be sized and shaped for inclusion in a breast implant. In some embodiments, the overall size and shape of transponder 100 may be minimized so as to potentially reduce any effect of the transponder on the size, shape, look, feel, or implantation process of an implant in which transponder 100 is installed. Minimizing the overall size and shape of transponder 100 may also assist in avoiding transponder interference with patient diagnostics, imaging procedures, and/or other medical procedures. Transponder 100 may also have an overall size and shape dictated in part by its components, as described in further detail below. For example, transponder 100 may have a long dimension, or length, determined in part by a size and shape of assembly 101, and in particular a size and shape of antenna 102.

In some embodiments, the long dimension, or length, of transponder 100 may measure between about 5 mm and about 30 mm, such as between about 5 mm and about 10 mm, between about 8 mm and about 13 mm, between about 10 mm and about 20 mm, between about 10 mm and about 15 mm, between about 12 mm and about 18 mm, between about 15 mm and about 20 mm, between about 15 mm and about 25 mm, between about 18 mm and about 26 mm, or between about 20 mm and about 30 mm. In some embodiments, transponder 100 may have a long dimension measuring about 8 mm, about 10 mm, about 13 mm, about 15 mm, about 18 mm, about 20 mm, about 23 mm, or about 25 mm.

In some embodiments, transponder 100 may have a width w, or short dimension perpendicular to the length (as seen in the top view of transponder 100 in FIG. 1A), measuring between about 1 mm and about 20 mm. For example, in some embodiments, transponder 100 may have a width measuring between about 2 mm and about 8 mm, between about 2 mm and about 5 mm, between about 2 mm and about 3 mm, between about 3 mm and about 6 mm, between about 5 mm and about 10 mm, between about 7 mm and about 12 mm, or between about 10 mm and about 15 mm. In some embodiments, transponder 100 may have a width, or short dimension, measuring about 1 mm, about 2 mm, about 3 mm, about 5 mm, or about 6 mm.

In some embodiments, transponder 100 may have a thickness, or short dimension perpendicular to both the width w and length of transponder 100, measuring between about 1 mm and about 20 mm. In some embodiments, for example, transponder 100 may have a thickness that is about the same as the width w of transponder 100. In further embodiments, for example, transponder 100 may have a thickness that is larger or smaller than that of width w of transponder 100.

In some embodiments, transponder 100 may be generally elongated in shape. For example, in some embodiments, transponder 100 may have a length which is more than twice as long as its width. Transponder 100 may have a length of about 13 mm and a width of about 2 mm, or a length of about 13 mm and a width of about 2.8 mm. In further embodiments, transponder 100 may have a length of about 13 mm and a width of about 2.2 mm. In further embodiments, transponder 100 may have a length of about 18 mm and a width of about 3 mm. An elongated shape may, for example, allow for ease of insertion of transponder 100 into a medical implant using, for example, a syringe into which transponder 100 may fit. An elongated shape may also, for example, be suitable for housing assembly 101 and, in particular, antenna 102, which are also elongated in shape.

In some embodiments, for example, transponder 100 may be generally cylindrical in shape. In such embodiments, the width of transponder 100 may be, for example, a diameter of the cylinder. In further embodiments, transponder 100 may be shaped as a rectangular prism, or any other shape. In some embodiments, transponder 100 may generally have few or rounded corners, in order to, e.g., reduce a risk of transponder 100 damaging an implant into which transponder 100 is installed. In further embodiments, transponder 100 may be a generally flat square shape, ovoid shape, or any other shape suitable for accommodating the components of transponder 100 and for placing the transponder 100 inside a medical device.

Assembly 101 of transponder 100 may include, for example, an antenna 102 and a chip 110, connected via antenna coil ends 108. Both antenna 102 and chip 110 of assembly 101 are described further below.

Antenna 102 may include, for example, antenna core 104 and antenna coil 106. In some embodiments, antenna coil 106 may be wound around antenna core 104. Antenna coil 106 may be made of a conductive, non-ferromagnetic material. In some embodiments, antenna coil 106 may be made of a material that may be able to withstand high temperatures (e.g., temperatures ranging up to about 250 degrees centigrade) for up to about 10,000 hours. In some embodiments, antenna coil 106 may be made of a metal wire, such as, e.g., copper wire or aluminum wire. In some embodiments, antenna coil 106 may be made of enameled wire, e.g., wire coated in a polymer. Suitable polymers may include, e.g., polyvinyl formal (Formvar), polyurethane, polyamide, polyester, polyester-polyimide, polyamide-polyimide (or amide-imide), and polyimide. In some embodiments, antenna coil 106 may be made of enameled copper wire, such as, e.g., Elektrisola enameled copper wire. In some embodiments, antenna coil 106 may be made of wire having a diameter ranging from about 0.010 mm to about 0.500 mm. For example, antenna coil 106 may be made of wire having a diameter of about 0.030 mm.

In some embodiments, antenna coil 106 may include tens to several thousand turns (i.e., loops) of wire. For example, in some embodiments, antenna coil 106 may include between about 30 to about 1500 turns of wire, such as between about 30 and about 100 turns, between about 100 and about 200 turns, between about 100 and about 400 turns, between about 100 and about 600 turns, between about 200 and about 500 turns, between about 300 and about 700 turns, between about 400 and about 600 turns, between about 500 and about 800 turns, between about 600 and about 900 turns, between about 800 and about 1000 turns, between about 800 and about 1200 turns, between about 1000 and about 1500 turns, and between about 1100 and about 1500 turns.

As depicted in FIGS. 1A-2B, antenna coil 106 may be wound in a longitudinal direction along a transponder axis A-A such that it has a longitudinal turn diameter t. Turn diameter t may be greater than the height of the coil h and/or the width of the coil x. Advantageously, this may, in some instances, allow for antenna coil 106 to, when induced, produce a stronger signal than an antenna coil which is wrapped such that it has a smaller longitudinal turn diameter t than its height h and/or width x (e.g., wrapped in a direction transverse to axis A-A). In some embodiments, antenna coil 106 may have a turn diameter t ranging from about 5 mm to about 20 mm, such as, for example, from about 5 mm to about 15 mm, from about 5 mm to about 12 mm, from about 5 mm to about 10 mm, from about 5 mm to about 7 mm, from about 6 mm to about 8 mm, from about 7 mm to about 10 mm, from about 9 mm to about 13 mm, from about 10 mm to about 15 mm, from about 12 mm to about 17 mm, from about 15 mm to about 19 mm, or from about 16 mm to about 20 mm. In some embodiments, antenna coil 106 may have a diameter of approximately 6 mm, 7 mm, 8 mm, 10 mm, 11 mm, 12 mm, or 13 mm.

In some embodiments, antenna coil 106 may have a height or thickness h, which may be less than the turn diameter t of antenna coil 106. The height (or thickness) h may generally be commensurate with the total thickness of the number of individual wire turns forming antenna coil 106. Height h may range, e.g., from about 0.2 mm to about 5 mm, such as, for example, from about 0.2 mm to about 0.5 mm, from about 0.2 mm to about 1 mm, from about 0.5 mm to about 1 mm, from about 0.5 mm to about 1.5 mm, from about 0.7 mm to about 1.2 mm, from about 0.7 mm to about 1.8 mm, from about 0.9 mm to about 1.4 mm, from about 0.9 mm to about 2 mm, from about 1 mm to about 1.5 mm, from about 1 mm to about 2.4 mm, from about 1.2 mm to about 1.8 mm, from about 1.4 mm to about 1.9 mm, from about 1.5 mm to about 2.0 mm, from about 1.8 mm to about 2.2 mm, from about 2 mm to about 2.4 mm, from about 2.2 mm to about 2.5 mm, from about 2.4 mm to about 2.8 mm, from about 2.5 mm to about 3 mm, from about 2.6 mm to about 3.5 mm, from about 2.8 mm to about 3.6 mm, from about 3 mm to about 4 mm, from about 3.5 mm to about 4.2 mm, or from about 3.8 mm to about 4.5 mm. In some embodiments, antenna coil 106 may have a height h of approximately, e.g., 1.5 mm, 1.7 mm, 1.9 mm, 2 mm, 2.1 mm, 2.2 mm, or 2.3 mm.

In some embodiments, antenna coil 106 may have an elongated shape, e.g. such that a turn diameter t of antenna coil 106 may be longer than, e.g., height h of antenna coil 106. In other embodiments, however, antenna coil 106 may have other shapes, such as, e.g., circular shapes, square shapes, etc.

Antenna core 104, around which antenna coil 106 may be wound, may be made of a biocompatible, non-conductive, non-ferromagnetic material. In other words, the material of antenna core 104 is neither attracted nor repelled by an externally-applied magnetic field. For example, antenna core 104 may be made of PEEK, ceramic, silica (glass), and/or another type of biocompatible plastic. In some embodiments, antenna coil 104 may be made of a material that may be able to withstand high temperatures (e.g., temperatures ranging up to about 250 degrees centigrade). Antenna core 104 may also be shaped in such a way that facilitates the shaping of antenna coil 106 around it. For example, as depicted in FIGS. 1A-2B, antenna core 104 may have notched ends 104e in which turns of wound antenna coil 106 may sit. In alternate embodiments, antenna core 104 may not have notched ends. Antenna core 104 may have dimensions configured to support a coil of a desired size and shape. For example, antenna core 104 may have a length around which antenna coil 106 may be wound, the length ranging from about 4 mm to about 20 mm, such as, for example, from about 4 mm to about 15 mm, from about 4 mm to about 10 mm, from about 5 mm to about 7 mm, from about 6 mm to about 8 mm, from about 7 mm to about 10 mm, from about 9 mm to about 13 mm, from about 10 mm to about 15 mm, from about 12 mm to about 17 mm, from about 15 mm to about 19 mm, or from about 16 mm to about 20 mm. In some embodiments, antenna core 104 may have a length of approximately 4 mm, 5 mm, 6 mm, 7 mm, 8 mm, 10 mm, 11 mm, 12 mm, 13 mm, or 14 mm.

In some embodiments, antenna core 104 may have a width perpendicular to the length of antenna core 104 (parallel to width x of antenna coil 106), and a thickness perpendicular to both the length and the width of antenna core 104 (parallel to height h of antenna coil 106). The width and the thickness of antenna core 104 may each range from about 0.5 mm to about 20 mm, such as, for example, from about 0.5 mm to about 15 mm, from about 0.5 mm to about 10 mm, from about 0.5 mm to about 5 mm, or from about 0.5 mm to about 3 mm. In some embodiments, each of the width and the thickness of antenna core 104 may be approximately 0.5 mm, 1 mm, 2 mm, or 3 mm.

In alternative embodiments, antenna 102 may simply include antenna coil 106 and no antenna core 104, such that antenna coil 106 is not wound around a solid object (e.g., it is an air coil surrounding air).

Chip 110 may be, for example, an integrated circuit (IC) chip. For example, in some embodiments of the present disclosure, chip 110 may be an application-specific integrated circuit (ASIC) chip, either with or without a built-in capacitor. In some embodiments, chip 110 may have, for example, printed circuit board (PCB) integration. In some embodiments, chip 110 may be an RFID chip. Chip 110 may be configured to sense, receive, and send a wide variety of data. In some embodiments, for example, chip 110 may be an ASIC designed to sense environmental conditions. For example, chip 110 may be a pressure ASIC. In further embodiments, chip 110 may be combined with one or more gauges configured to sense environmental conditions, such as a physical strain gauge, a pressure gauge, or a temperature gauge. In some embodiments, chip 110 may be an ASIC or other type of chip programmed with identifying data, such as a serial number, such that when provided with power, chip 110 will return such identifying data. Additional examples of sensors and information which may be paired or associated with chip 110 are described further herein.

Although one chip 110 is depicted, in some embodiments, two or more chips may also be used in assembly 101. In such cases, the two or more chips may each share a single functionality, or may each carry a distinct functionality, e.g., each may carry different identifying information or may be paired with different sensors.

Chip 110 may include bond pads 112, which may be used to connect chip 110 with antenna coil ends 108. Bond pads 112 may, for example, be embedded into an etched surface of chip 110 such that they do not protrude from the surface of chip 110. Bond pads 112 may be, for example, made out of a nonmagnetic metal, such as, for example, gold.

Antenna coil ends 108 may be connected to bond pads 112 via, for example, thermal compression, laser welding, soldering, or a crimp connection. Alternately, antenna coil ends 108 may be connected to bond pads 112 by other methods known in the art, such as using a conductive adhesive.

Capsule 114 may enclose assembly 101, as well as an inner space 116 surrounding assembly 101. Capsule 114 may be made from, for example, a biocompatible material, such as glass (e.g., silicate glass, such as a soda-lime silicate glass), or a biocompatible plastic. Capsule 114 may be the outermost portion of transponder 100, and may therefore have a size and shape corresponding to a desired size and shape of transponder 100. Exemplary sizes and shapes of transponder 100 have been previously disclosed herein. Capsule 114 may, for example, include two pieces, which may be assembled around assembly 101.

Inner space 116 may be a vacuum, or may contain air, a liquid, solid, or gel material. In some embodiments, inner space 116 may be fully or partially filled with a liquid, solid, or gel material. For example, in some embodiments, inner space 116 may be filled with a liquid, solid, or gel material configured to provide transponder 100 with shock resistance. In some embodiments, inner space 116 may be fully or partially filled with an adhesive, such as, e.g., a glue. In such embodiments, the glue may be a biocompatible adhesive, such as an epoxy or an acrylate adhesive. In some embodiments, the glue may be a photoinitated-curing acrylate adhesive. In some embodiments, the glue may be a shock-resistant glue. In some embodiments, the glue may be a glue that may be exposed to temperatures of up to about 250 degrees centigrade, and after cooling to room temperature may have a similar or the same temperature, viscosity, and other characteristics as it had before being exposed to the temperatures of up to about 250 degrees centigrade.

In some embodiments, half of inner space 116 may be filled with a liquid, solid, or gel material, such as an adhesive as described above. In other embodiments, at least 30% of inner space 116 may be filled. In other embodiments, between about 30% and about 50% of inner space 116 may be filled. In further embodiments, over 60% of inner space 116 may be filled. In further embodiments, between about 50% and about 100% of inner space 116 may be filled, such as about 55%, about 65%, about 75%, about 85%, about 90%, about 95%, or about 100% of inner space 116. In yet further embodiments, between about 80% and about 100% of inner space 116 may be filled. In some embodiments, about 90% or more of inner space 116 may be filled. In yet further embodiments, about 95% or more of inner space 116 may be filled.

Multiple configurations of transponders according to the present disclosure may be based on exemplary transponder 100. For example, chip 110 may have a variety of configurations and specifications, depending on the availability of chips in the art. Based on, e.g., the type of chip used, the configuration of a transponder according to the present disclosure may change.

One example of an alternative embodiment of transponder 100 is depicted in FIGS. 2A and 2B.

FIGS. 2A and 2B depict, in schematic form, a top-down view (FIG. 2A) and a side view (FIG. 2B) of transponder 200, which may be another configuration of a transponder according to the present disclosure. In transponder 200, an assembly 118 may include antenna 102, chip 110, a capacitor 120 external to chip 110, and a base 122 to which the chip 112 and the capacitor 120 may be attached. Antenna coil ends 108 of antenna coil 106 may extend through base 122, or may attach to an electrical conductor extending through base 122, to positive and negative leads of capacitor 120 so as to create a circuit with capacitor 120. Wires 123 may connect capacitor 120 to bond pads 112 of chip 110. A capsule 124 may enclose assembly 118 and inner space 116 surrounding assembly 118.

Capacitor 120 may be included in transponder 200, separate from chip 110. In transponder 200, chip 110 may or may not include a built-in capacitor. As depicted in FIGS. 2A and 2B, assembly 118 of transponder 200 may include base 122, to which capacitor 120 and chip 110 may be installed, and to which antenna coil ends 108 of antenna 102 may be attached. Base 122 may provide, for example, stability and structure to assembly 118, and may also, as depicted, serve as a medium through which the capacitor 120 may be connected to antenna coil ends 108 of antenna 102, as well as chip 110.

Base 122 may be made of any non-ferromagnetic, biocompatible material, such as, e.g., any material suitable for use in forming antenna core 104 (e.g., PEEK or other biocompatible plastic). Additionally, base 122 may, in some embodiments, include conductive elements through which antenna 102, capacitor 120, and/or chip 110 may be connected. For example, in some embodiments, base 122 may include conductive tracks or pads configured to support connections between antenna coil ends 108, capacitor 120, and chip 110. In some embodiments, a portion or all of base 122 may be a circuit board, such as, e.g., a printed circuit board.

As depicted schematically in FIGS. 2A and 2B, antenna coil ends 108 may be attached to base 122 by, for example, thermal compression, welding, soldering, a crimp connection, or other known attachment types. Similarly, capacitor 120 may be connected to base 122 by, e.g., thermal compression, welding, soldering, etc. A connection may extend through base 122 from one attached antenna coil end 108 to a positive lead of capacitor 120, and from the other attached antenna coil end 108 to a negative lead of capacitor 120. Capacitor 120 may further be connected to chip 110, which may also be attached to base 122 by, for example, wires 123 attached to bond pads 112 via thermal compression, welding, soldering, a crimp connection, or other attachment types known in the art.

In yet further embodiments, assembly 118 of transponder 200 may not include base 122. In such embodiments, antenna coil ends 108 may be directly connected to capacitor 120 by, for example, thermal compression, welding, soldering, a crimp connection, or the like, and capacitor 120 may likewise be connected to chip 110. As with transponder 100, antenna 102 in transponder 200 may or may not include antenna core 104.

In the embodiments depicted in FIGS. 2A and 2B, capsule 124 may be similar in construction to capsule 114. In some embodiments, depending on the size and shape of capacitor 120, capsule 124 may need to be larger than capsule 114, in order to accommodate capacitor 120. Similarly, inner space 124 of transponder 200 may be larger than inner space 116 of transponder 100. Inner space 124 may be a vacuum, or may be filled with a variety of substances, as has been disclosed with respect to inner space 116.

In some embodiments of transponders according to the present disclosure (e.g., transponders 100, 200), the transponders may not be enclosed in a capsule, e.g., having an inner space. Instead, in some embodiments, transponders (e.g., transponders 100, 200) may just include components of, e.g., assemblies 101, 118.

In some embodiments of transponders according to the present disclosure, a chip of the transponder (e.g. chip 110) may not have a built-in capacitor. In such embodiments, a capacitor external to chip 110 (e.g. capacitor 120) may serve as primary electrical energy storage for 120 to, for example, power a chip, such as chip 110. In further embodiments, such as embodiments in which a chip (e.g., chip 110) does have a built-in capacitor, the added capacitor (e.g., capacitor 120) may provide additional power to the chip, so that the chip may be powered for a longer period of time or may be supplied a greater amount of power than with simply a built-in capacitor internal to, e.g., chip 110. Added capacitor 120 in transponder 200 may, for example, allow transponder 200 to store a greater amount of electrical energy than a transponder without capacitor 120.

Transponders according to the present disclosure (such as, e.g., transponders 100, 200 depicted in FIGS. 1A-2B) may be, for example, configured to transmit data via low wavelength RF coupling communication. For example, data may be communicated via RF low wave transmissions having a frequency ranging from about 100 kHz to about 400 kHz, such as, e.g., from about 200 kHz to about 300 kHz, from about 100 kHz to about 200 kHz, from about 120 kHz to about 150 kHz, from about 125 kHz to about 145 kHz, or from about 130 kHz to about 135 kHz. In some aspects, the communication frequency of assembly 101 may be about 134.2 kHz.

Transponders according to the present disclosure, such as transponders 100, 200, may be adapted for temporary or permanent implantation with an implantable medical device. For example, one or more transponders according to the present disclosure may be partially or fully enclosed in a biocompatible material, and integrated into the medical device. Exemplary biocompatible materials include silicone and other polymers and polymer coatings suitable for temporary or permanent medical implantation. In some aspects of the present disclosure, a transponder may be placed between two portions of silicone that form a biocompatible envelope around the transponder.

Transponders according to the present disclosure (e.g., transponders 100, 200) may be incorporated into an interior space of a medical device, or attached to an inner or outer surface of the medical device. In some aspects, the medical device may be a breast implant or tissue expander, and the transponder(s) may be suspended inside the breast implant or tissue expander. In other aspects, the transponder(s) may be attached to an inner or outer surface of a shell or outer wall of the breast implant or tissue expander, or may be incorporated into a shell or wall of the breast implant or tissue expander, for example between layers comprising the shell or wall of the breast implant or tissue expander. In at least one example, the transponder(s) may be permanently attached or encased in a silicone plastic case and integrated into a tissue expander or medical implant by dielectrically sealing or bonding the encased transponder(s) to the shell of the tissue expander or medical implant. In some examples, the transponder(s) encased in silicone may be placed into an inner volume of the tissue expander or medical implant, e.g., such that the transponder(s) is/are free floating in the inner volume or suspended in a material filling the inner volume of the tissue expander or medical implant.

According to some aspects of the present disclosure, a medical device may include a plurality of transponders (e.g., transponders 100, 200), e.g., 2, 3, 4, 5, or 6 or more transponders. Each transponder may be spaced apart from the other sensor(s) in a predetermined spacing interval. Such combinations of transponders in a medical device may be useful for determining orientation information, such as changes in orientation of the medical device, displacement of the medical device, changes in an amount of material between the transponders, and/or changes in a physical or chemical property of the material between the transponders. Such changes may be determined, for example, by measuring impedance between two or more transponders.

Further, for example, two or more medical devices implanted in a patient may include transponders with the ability to communicate and/or provide information relevant to each other. For example, for a patient with two breast implants, each implant may include one or more transponders in communication with the transponder(s) in the other implant. Additionally, or alternatively, the transponder(s) of each implant may be configured to provide data in reference to a common anatomical feature of the patient and/or a common reference point of one of the implants.

Transponders 100, 200 may, for example, be active, passive, or both active and passive. In cases of permanent implants or medical devices intended for a relatively long-term implantation, passive transponders may avoid concerns of recharging power cells, cycle life, and/or possible corrosive properties of certain materials (e.g., dissimilar materials) that may be used in the design of batteries for active sensors. Data may be transmitted, received, stored and/or analyzed by the transponders either actively and/or passively. For example, data may be transmitted via radiofrequency from a transponder to an external reader (external to the implant) configured to receive and/or analyze or otherwise process the data. Exemplary embodiments of such readers are disclosed further herein. Such a reader may be implanted within the patient, or may be external to the patient and attached or not attached to the patient. According to some aspects of the present disclosure, data may be transferred between a transponder (e.g., transponder 100, 200) and a reader within a distance of about 10 feet separating the transponder from the reader, e.g., a distance of about 7 feet, about 5 feet, about 3 feet, or about 1 foot. For example, in some aspects of the present disclosure, the transponder (e.g., transponder 100, 200) may be configured to send and/or receive information within a range of from about 1 inch to about 5 feet, from about 2 inches to about 3 feet, from about 3 inches to about 1 foot, from about 2 inches to about 9 inches, from about 4 inches to about 8 inches, or from about 4 inches to about 6 inches.

Transponders (e.g., transponders 100, 200) may be configured to detect and/or measure various stimuli or parameters. For example, transponders according to the present disclosure may be configured to detect and/or measure one or more of acoustic data, temperature, pressure, light, oxygen, pH, motion (e.g., accelerometers), cyclo-rotation (e.g., gyro sensors), or any other physiological parameter, using sensors known in the art coupled to a chip of a transponder, e.g., chip 110 of transponders 100, 200. For example, an exemplary pH sensor may include a measuring electrode, a reference electrode, and a temperature sensor. The sensors may include a preamplifier and/or an analyzer or transmitter to assist in displaying the data. In some aspects, the sensors may be configured to determine the location and orientation of an implanted medical device, e.g., to assess any improper changes in location or orientation after initial implantation.

The sensors may be calibrated with an appropriate reference or standard in order to provide an accurate measurement value, or absolute or relative change in values. For example, temperature sensors may be calibrated according to one or more reference temperatures, and pressure sensors may be calibrated to indicate a change in pressure.

In some examples, the implantable medical device may include a transponder and/or sensor package comprising a transponder in combination with one or more other transponders, sensors, and/or additional electronic components. The transponder(s), sensor(s), and electronic components may be coupled together or otherwise in communication with each other. For example, an exemplary transponder and/or sensor package may include one or more transponders coupled to one or more sensors for measuring pressure, temperature, acoustic data, pH, oxygen, light, rotational movement or cycles, or a combination thereof. A transponder and/or sensor package may comprise individual integrated circuits coupled together via a PCB or fully integrated into an ASIC.

The transponders (e.g., transponders 100, 200) of the present disclosure may be read/write, e.g., where data may be written into or otherwise associated with each transponder by a user in order to be read by a suitable device, such as an external reader. Such data may include a unique device identifier for the transponder, the transponder and/or sensor package, and/or the medical device. Information provided by the unique device identifier may include, e.g., serial number(s), manufacturer name(s), date(s) of manufacture, lot number(s), and/or dimensions of the medical device and/or sensor(s). For example, one or more transponders (e.g., transponders 100, 200) associated with a breast implant may include information on the implant's dimensions (e.g., size and/or volume), manufacturer, date of manufacture, and/or lot number. Additionally, or alternatively, the one or more transponders (e.g., transponders 100, 200) associated with the breast implant may include information on the transponder(s) and/or sensor(s) paired with the one or more transponder(s), such as the type of data collected/measured, manufacturer, date of manufacture of the implant, and/or serial number(s) of the implant and/or implant package, the type, dosage, and/or composition of ancillary coatings or materials used in association with the implant, etc.

Integration of acoustic sensors with transponders (e.g., transponders 100, 200) into implantable medical devices may enhance auscultation, e.g., allowing for monitoring and/or examining the circulatory system (e.g., via heart sounds relating to cardiac output or structural defects/disorders), respiratory system relating to pulmonary function (e.g., via breathing sounds), and/or the gastrointestinal system relating to obstructions and ulcerations (e.g., via bowel sounds). The acoustic sensors may include lever and MEMS (microelectromechanical system) devices. Examples of acoustic sensors that may be used herein include, but are not limited to, accelerometers (e.g., measuring vibrational noise), thermal sensors (e.g., measuring thermomechanical noise), and piezocapative sensors, among other types of acoustic sensors. The acoustic sensors may operate manually when provided power (e.g., when a transponder paired with the sensors is coupled with a reader). Capacitors (e.g., capacitor 120 in transponder 200, or a built-in capacitor in chip 110) and/or batteries may allow a transponder (e.g., transponder 100, 200) to gain information and store the information and transfer data when asked or coupled to another electronic device.

Further, transponders according to the present disclosure may be configured to enhance acoustic data. Enhancing acoustic sounds may include algorithms that are trained with known sounds to give reference as to an amount or degree of change, and/or for elimination of non-significant noise (e.g., signals that may be an artifact of measurement technique) that may interfere with the generation of "clean" signals providing meaningful information about the patient. Such algorithms may be loaded onto a chip (e.g., chip 110) of a transponder (e.g., transponders 100, 200).

As mentioned above, transponders such as transponders 100, 200 may be configured to communicate with an external reader for processing the data, e.g., by filtering noise from raw data. For example, the transponders may be used in combination with algorithms that collate and analyze filtered data, e.g., taking in raw data from the sensors at a minimal transmission (threshold) format based on pre-programmed parameters (e.g., data obtained from reference tables). Such algorithms may be designed to combine relevant integrated data specific to provide a proper signal indicative of a mechanical or clinical problem, which then may be processed by a reader. Readers are described in further detail elsewhere in this disclosure. The reader may include a graphic display such as an LED display, and may have parameters established in the firmware of the reader to present the data output on the display and/or provide a notification signal. For example, the notification signal may be a recommendation displayed on the reader that the patient contact his/her caregiver or clinician to follow up on a particular action item. For example, the reader may suggest examination or modification of a particular aspect of the implanted medical device (e.g., add more saline solution to a tissue expander via a syringe, etc.).

Further uses, systems, and combinations of transponders, sensors, and readers, are also disclosed elsewhere herein.

Integrated Port Assemblies and Locator Coils

The present disclosure also includes low artifact transponders that may be used in order to locate particular parts or characteristics of implanted medical devices. For example, some implanted medical devices may require alteration or adjustment after implantation. As an example, tissue expanders may be used during breast reconstruction or augmentation surgery in order to incrementally expand chest tissue over time, so that the tissue is able to accommodate a more permanent implant. Tissue expanders according to the present disclosure may also be used for procedures other than breast augmentation and reconstruction.

Tissue expanders may be inflated manually and/or electronically, e.g., with a syringe or other suitable device for introducing and withdrawing a fluid (e.g., a liquid or gaseous fluid) or gel into the tissue expanders. The tissue expanders may be inflated with saline solution, which may be supplied in a sterile pouch, such as the Hydropac® products by Lab Products, Inc. In some aspects, inflation may be performed wirelessly, e.g., by communicating with an internal chamber or cylinder of compressed air.

According to some aspects of the present disclosure, the tissue expander may include one or more pressure sensors and/or one or more strain gauges, which may be coupled with, e.g., transponders (e.g., transponders 100, 200). Such sensors may allow for the continuous and/or intermittent measuring of pressure to optimize, regulate, and/or wirelessly control the expansion and deflation of such tissue expanders. A transponder/sensor package for a tissue expander (including, e.g., sensors for measuring pressure, temperature, acoustic data, pH, oxygen, light, or a combination thereof) may be contained in a silicone molded enclosure. In at least one example, the tissue expander may include at least one of a pressure sensor or a strain gauge coupled to, or embedded in, the outer wall (shell) of the tissue expander. In some aspects, the tissue expander may include a sensor/transponder package (including, e.g., sensors for measuring pressure, temperature, acoustic data, pH, oxygen, light, or a combination thereof), which may have a fixed location relative to the tissue expander. Such sensor/transponder packages may be paired with readers, which are described in further detail elsewhere in this disclosure.

A tissue expander may include a port, through which fluids may be injected into the tissue expander after the tissue expander has been implanted into a patient. A port may be located within an aperture in a shell of a tissue expander, the aperture being sized specifically to fit the port. Thus, the port may be implanted along with a tissue expander and may not be immediately detectable from the exterior of the patient. Advantageously, transponders and/or coils according to the present disclosure may be combined with, for example, tissue expander ports and valve assemblies, in order to assist in detection of the ports and valve assemblies. By having a transponder and/or antenna coil installed within a tissue expander port or valve assembly, a physician may be able to noninvasively identify the appropriate location of a port in order to inject saline solution into a patient in whom the tissue expander is implanted. As with transponders 100, 200, such transponders, antenna coils, and/or valve assemblies may be made of materials that are alternatives to ferromagnetic materials, which can cause an imaging artifact under magnetic resonance imaging. For example, the transponders, coils, and/or and associated valve assemblies disclosed herein may comprise non-ferromagnetic materials, such as poly-ether-ether-ketone (PEEK) or other plastics.

Figure 3A:
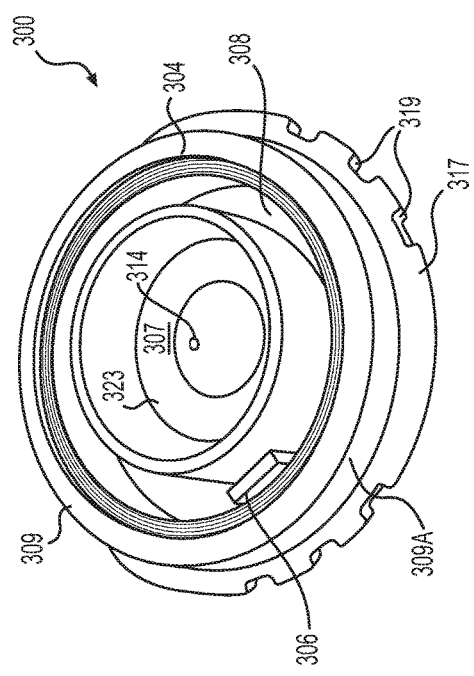
Figure 3C:
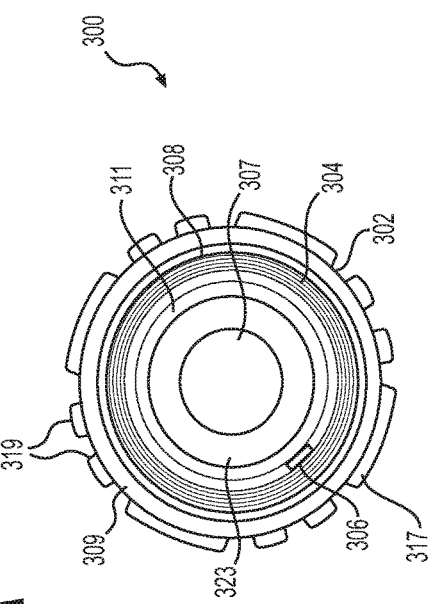

FIGS. 3A-3C show an exemplary valve assembly 300 according to the present disclosure, including a casing 302, a coil 304, and a chip 306 connected to coil 304. FIG. 3A depicts a three-dimensional view of valve assembly 300, FIG. 3B depicts a side view of valve assembly 300, and FIG. 3C depicts a top-down view of valve assembly 300. Casing 302 may have a circular well portion 308 in which coil 304 and chip 306 are housed. Well portion 308 may have a lip 309 of a wall 309A which protrudes inward over well portion 308. Casing 302 may also include an inner chamber 307 centered within well portion 308 and surrounded by a wall 311. A circumferential inner ledge 323 may protrude into inner chamber 307. As depicted in FIG. 3B, a portion of inner chamber 307 may extend to a deeper depth than well portion 308, such that casing 302 has a center portion 312 that protrudes into a medical implant (e.g., a tissue expander) from the rest of casing 302. Center portion 312 may have a reinforced tip 315 at the furthest end of its protrusion. One or more fluid holes 314 may pass from inner chamber 310 through center portion 312. Casing 302 may also have a circumferential outer ledge 317 around wall 311. Outer ledge 317 may include one or more notches 319.

Valve assembly 300 may be configured for installation in a shell of a tissue expander. Valve assembly 300 may be made of a biocompatible, non-magnetic, non-ferromagnetic material, such as, for example, molded PEEK. Valve assembly 300 may be of a hardness sufficient to prevent being pierced by a cannula, such as the cannula of a syringe used to inject fluid into a tissue expander in which valve assembly 300 is installed. Valve assembly 300 may be sized and shaped to allow for a coil 304 to fit within a circumference of valve assembly 300.

Coil 304 may be a wound radiofrequency (RF) antenna coil made of, e.g., a metal wire, such as, e.g., copper wire or aluminum wire. In some embodiments, coil 304 may be made of enameled wire, e.g., wire coated in a polymer. Suitable polymers may include, e.g., polyvinyl formal (Formvar), polyurethane, polyamide, polyester, polyester-polyimide, polyamide-polyimide (or amide-imide), and polyimide. In some embodiments, coil 304 may be made of enameled copper wire, such as, e.g., Elektrisola enameled copper wire.

Coil 304 may be sized and shaped so as to frame a core, or center portion, through which a cannula may pass into a central chamber 307 of valve assembly 300. Coil 304 may also be sized and shaped so as to be detected by, e.g., a reader configured to detect the center of the wound coil. In this manner, coil 304 may serve as, e.g., a "targeting element" for a reader being used to search for a valve assembly, e.g., valve assembly 300. In some embodiments, coil 304 may have a regular hollow cylindrical shape, and may have an outer diameter, e.g., ranging from about 10 mm to about 50 mm, such as, for example, from about 10 to about 40 mm, from about 15 mm to about 35 mm, from about 15 mm to about 25 mm, from about 20 mm to about 35 mm, or from about 22 to about 27 mm. In some embodiments, for example, coil 304 may have an outer diameter of about 24 mm, about 24.6 mm, about 25 mm, about 25.3 mm, about 26 mm, or about 26.2 mm.

In some embodiments, coil 304 may have an inner diameter, e.g., ranging from about 10 mm to about 50 mm, such as, for example, from about 10 mm to about 40 mm, from about 10 mm to about 35 mm, from about 15 mm to about 35 mm, from about 15 mm to about 30 mm, from about 15 mm to about 25 mm, or from about 18 mm to about 22 mm. In some embodiments, for example, coil 304 may have an inner diameter of about 18 mm, about 19 mm, about 19.5 mm, about 20 mm, about 20.1 mm, about 20.3 mm, about 20.4 mm, about 20.5 mm, about 20.6 mm, about 20.7 mm, about 21 mm, or about 22 mm.

In some embodiments, coil 304 may have a height ranging from about 1 mm to about 20 mm, such as from about 1 mm to about 15 mm, from about 1 mm to about 13 mm, from about 1 mm to about 10 mm, from about 1 mm to about 8 mm, from about 1 mm to about 5 mm, or from about 1 mm to about 4 mm. For example, in some embodiments, coil 304 may have a height of about 1 mm, about 2 mm, about 2.1 mm, about 2.2. mm, about 2.5 mm, about 2.7 mm, about 2.8 mm, about 2.9 mm, about 3 mm, about 3.2 mm, about 3.4 mm, about 3.6 mm, about 3.8 mm, about 3.9 mm, or about 4.0 mm.

Coil 304 may be formed of any number of turns sufficient to be induced by an external reader (e.g., reader 800, which is described further herein). For example, in some embodiments, coil 304 may be formed of between about 10 and about 2000 turns. In some embodiments, for example, coil 304 may be formed of between, e.g., about 100 and about 1500 turns, about 500 and about 1100 turns, or about 800 and about 1000 turns. In some embodiments, for example, coil 304 may be formed of, e.g., about 500, about 700, about 800, about 1000, about 1100, or about 1200 turns.

Chip 306 may be an RF chip known in the art, such as, e.g., chips that have been described elsewhere herein (e.g., chip 110). Generally, disclosures herein with respect to chip 110 may apply with respect to chip 306 as well. In some embodiments, for example, chip 306 may be an ASIC. Chip 306 may or may not include a capacitor. In some embodiments, chip 306 may be an ASIC programmed with identifying data, such as a serial number, such that when provided with power, chip 110 will return such identifying data. In some embodiments, chip 306 may be a sensor, or may be paired with sensors, as has been described elsewhere herein with respect to chip 110. In alternate embodiments of valve assembly 300, there may be no chip 306. In such cases, coil 304 may be used primarily as a targeting element for assisting in locating valve assembly 300.

Casing 302 of valve assembly 300 may be sized and shaped to accommodate coil 304 and chip 306 in well portion 308, as well as inner chamber 307. Well portion 308 of valve assembly 300 may have a generally circular shape, in order to accommodate coil 304 and, e.g., chip 306 connected to coil 304. Well portion 308 of valve assembly 300 is depicted as being open in FIGS. 3A-3C; however, in some embodiments, circular well portion 308, containing coil 304 and chip 306, may be closed and sealed off from the rest of valve assembly 300 by, e.g., a biocompatible material, such as a biocompatible material from which the body of casing 302 is made (e.g., PEEK), or another biocompatible material (e.g., silicone).

Lip 309, which may protrude over well portion 308, may be configured to interlock with, e.g., a dome that may cover valve assembly 300. Such a dome may be, for example, integrated port dome 310, which is shown in, e.g., FIG. 4, and is described further herein. In alternate embodiments, lip 309 may protrude in a different direction (e.g., outward and away from well portion 308), or may include intermittent protrusions for attachment to, e.g., a dome that may cover valve assembly 300 in a different manner.

Inner chamber 307 is radially inward of coil 304 and well 308. Inner chamber 307 may, in some embodiments, be cylindrical-shaped, bowl-shaped, or both. In some embodiments, inner chamber 307 may have a depth that is deeper than, e.g., well portion 308, such that some or all of inner chamber may extend into center portion 312, which may protrude below the rest of casing 312 (e.g, well portion 308), as depicted in, e.g., FIGS. 3B and 4. Inner chamber 307 may be configured to receive, e.g., fluid from, e.g., a cannula, syringe, or other fluid injection device. Fluid holes 314 may extend from inner chamber 307 through casing 302 and out center portion 312, such that fluid may pass from inner chamber 307 through fluid holes 314 and into, for example, a medical implant into which valve assembly 300 is installed. In some embodiments, fluid holes 314 may include valves, e.g., one way valves (e.g., duck bill valves), configured to allow fluid to pass from inner chamber 307 outward into, e.g., a medical implant, and not back into inner chamber 307. A bottom surface of inner chamber 307 may be reinforced by inner tip 315, so as to prevent penetration by, e.g., a cannula, syringe, or other injection means.

Figure 4:
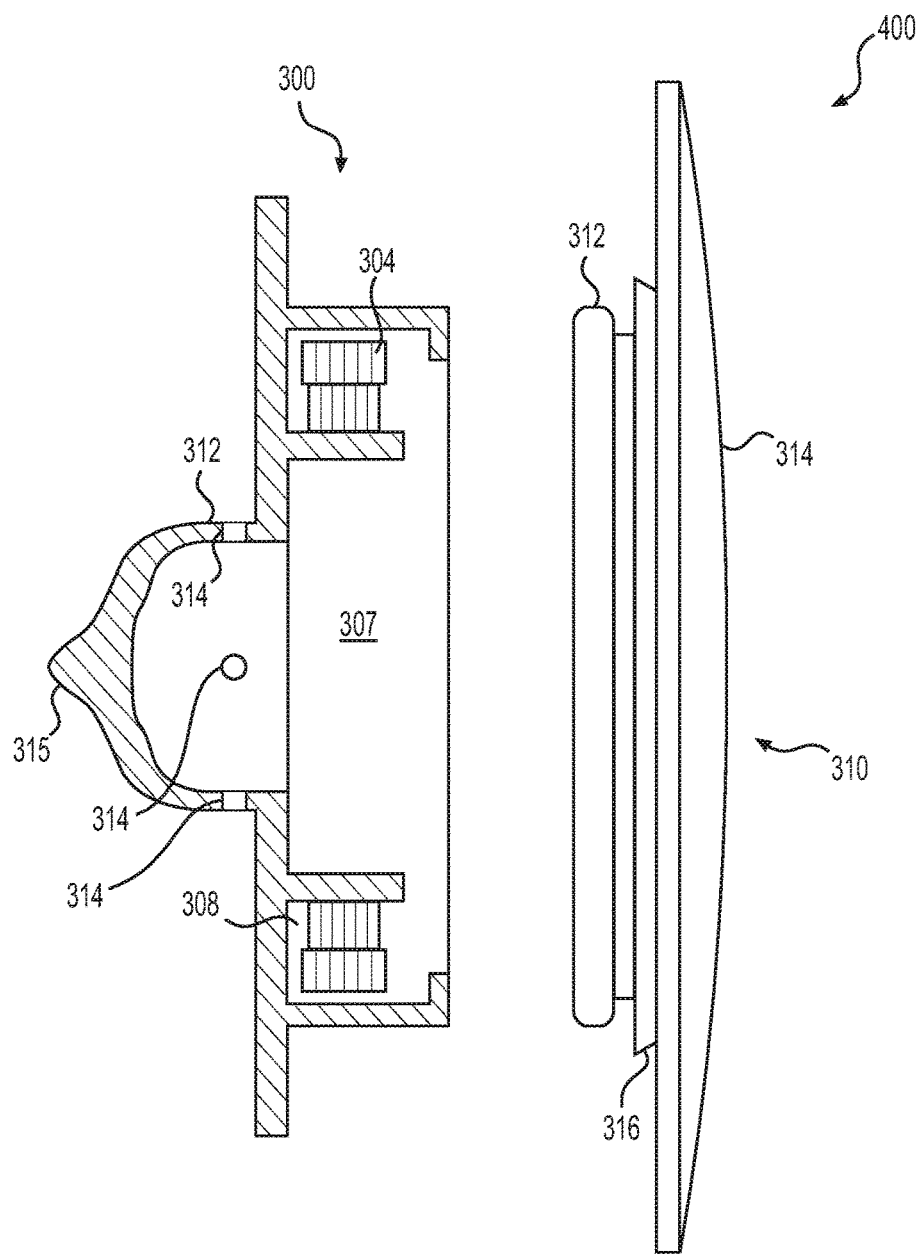
FIG. 4 shows another view of an exemplary valve assembly, according to some aspects of the present disclosure.

FIG. 4 depicts a side view of an integrated port assembly 400, which may include valve assembly 300 (of which a cross-sectional view is presented), and an integrated port dome 310. Integrated port dome 310 may include a step 316, which may be configured to fit against the edges of an aperture in a wall of an implant into which integrated port assembly 400 may be installed, so that patch portion 314 sits over the implant wall. Integrated port dome 310 may also have a flange 312, which may be configured to interlock with lip 309 of valve assembly 300, thus connecting valve assembly 300 to integrated port dome 310. Patch portion 314 is wider than flange 312 and valve assembly 300.

Integrated port dome 310 may be made of a biocompatible material suitable for interfacing with patient tissue, as well as with a surface of an implant into which integrated port assembly 400 may be installed. Some or all of integrated port dome 310 may be made of a material that is penetrable by, e.g., a cannula, syringe, or other injection device, such that an injection device may penetrate integrated port dome 310 and inject fluid within inner chamber 307 of valve assembly 300. In some embodiments, integrated port dome may be made of a self-sealing material, such that when integrated port dome 310 is penetrated by an injection device and the injection device is subsequently removed, integrated port dome will seal the penetration site and prevent fluids from escaping valve assembly 300. In some embodiments, integrated port dome 310 may be made of a silicone material. In some embodiments, for example, integrated port dome 310 may be made of a silicone material which may be vulcanized.

Integrated port dome 310 may be sized and shaped to, e.g., interlock securely with valve assembly 300. As depicted in, e.g., FIGS. 5B and 5C, described further below, flange 312 of integrated port dome 310 may be further sized and configured to cover any opening in well portion 308 of valve assembly 300, when interlocked with lip 309 of valve assembly 300, thus sealing coil 304 (and chip 306) within well 308 and preventing the exposure of coil 304 and chip 306 to fluids.

FIGS. 5A, 5B, and 5C depict integrated port assembly 400 installed in an exemplary implant shell 500. Implant shell 500 may be, for example, a shell of a tissue expander, as depicted in FIG. 5A. In some embodiments, implant shell may be made of silicone; however, implant shells of any biocompatible material may be used in conjunction with integrated port assembly 400. Integrated port assembly 400 may be installed in an aperture 502 of implant shell 500. Valve assembly 300 of integrated port assembly may be located inside implant shell 500. Integrated port dome 310 may be attached to valve assembly 300, and patch portion 314 may be located outside implant shell 500. In FIG. 5A, patch portion 314 of integrated port dome 310 is depicted by a dotted line, showing how integrated patch portion 314 may overlap with some surface area of implant shell 500. Other portions of integrated port dome 310 are not depicted, so as to depict valve assembly 300. In some embodiments, patch portion 314 and implant shell 500 may be attached to one another, e.g., by vulcanization, adhesion, or other method.

FIG. 5B depicts a cross-sectional view of integrated port assembly 400 installed in implant shell 500. As depicted in FIG. 5B, an edge of aperture 502 of implant shell 500 may be angled in a manner complementary to an angle of step 316 of integrated port dome 310, so as to fit snugly against step 316. In such a manner, and in combination with the overlap and attachment of patch portion 314 with implant shell 500, integrated port assembly 400 may be sealed and secured within aperture 502 of implant shell 500.

FIG. 5C depicts the same cross-sectional view of integrated port assembly 400 installed in implant shell 500 as FIG. 5B. FIG. 5C also depicts how an exemplary cannula 504 may penetrate integrated port dome 310 to reach inner chamber 307. Cannula 504 may be configured to deliver fluid into inner chamber 307, and subsequently to the inside of implant shell 500. As has been previously described, integrated port dome 310 may be made of a self-sealing material, such as a silicone material, such that when cannula 504 is withdrawn, integrated port dome 310 seals fluid within inner chamber 307 and implant shell 500.

Figure 6:
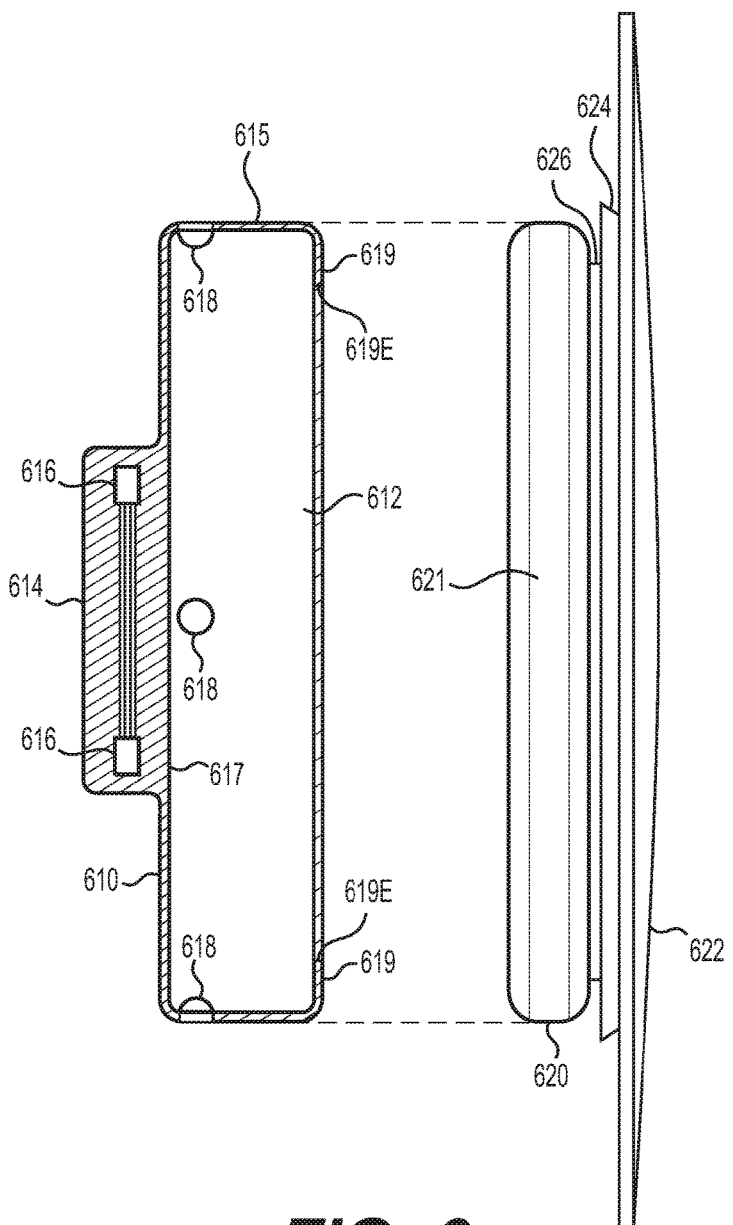
FIG. 6 shows another exemplary integrated port valve assembly, according to some aspects of the present disclosure.

FIG. 6 depicts another exemplary integrated port assembly 600, which may include a valve assembly 610 and an integrated port dome 620. Valve assembly 610 may include a main chamber 612 surrounded by a wall 615 having a lip 619. Lip 619 has an inner edge 619 E. Main chamber 612 may have a top opening defined by edge 619E configured to face integrated port dome 620, and may accommodate a plug 621 of integrated port dome 620. Wall 615 of main chamber 612 may have one or more fluid holes 618 that may pass from main chamber 612 out of the valve assembly 610. A coil 616 may be located in a coil housing 614 which is separated from main chamber 612 by a needle stopping surface 617, such that coil 616 is centered beneath main chamber 612. Integrated port dome 620 may have a patch 622, which may have a wider width than plug 621 and valve assembly 610, and may be integral with plug 621. A flange 626 between patch 622 and plug 621 may be configured to accommodate and interlock with lip 619 of valve assembly 610. Integrated port dome 620 may also have a step 624 configured to interface with a wall of an implant into which the integrated port assembly 600 may be installed.

Aspects of integrated port assembly 600 may, in general, be similar to aspects of integrated port assembly 400. For example, in some embodiments, valve assembly 610 may be made of any of the materials out of which valve assembly 300 may be made, such as biocompatible, non-ferromagnetic materials, such as PEEK. Further, main chamber 612 of valve assembly 610 may have a function similar to inner chamber 307 of valve assembly 300, in that main chamber 612 may be sized, shaped, and configured to receive fluids from, e.g., a cannula, syringe, or other fluid deposition device. An inner surface 617 of main chamber 612 may be configured to prevent or resist puncturing by, e.g., a cannula depositing fluid within main chamber 612. For example, inner surface 617 may be made of a material having a density, hardness, or thickness configured to prevent or resist puncturing by a fluid deposition device. In some embodiments, main chamber 612, including inner surface 617, may be made of biocompatible PEEK.

Coil 616 may be similar, in terms of size, shape, configuration, materials, and construction, to coil 304, which has previously been disclosed above with respect to FIGS. 3A-5C. Coil 616 may be housed in a coil housing 614. In some embodiments, coil housing 614 may be sealed shut, such that no fluids may enter or exit coil housing 614. In some embodiments, coil housing may be cylindrical, as shown, and may be coaxial with main chamber 612, such that coil 616 is also coaxial with main chamber 612. In this manner, the location of coil 616 may be used to locate the center, or the approximate center, of main chamber 612. Coil housing 614 is depicted as having a smaller circumference than, e.g. main chamber 612. However, in some embodiments, coil housing 614 may have a circumference that is as large as, or nearly as large as, main chamber 612.

Though not pictured, coil 616 may be coupled to a chip, similar to chip 306 connected to coil 304. Such a chip may have any of the characteristics and capabilities of chips that are otherwise disclosed herein.

Integrated port dome 620 may be similar in shape, structure, and construction materials to integrated port dome 310 of integrated port assembly 400. For example, plug 621 of integrated port dome 620 may be sized and shaped to snugly interlock with, e.g., lip 619 of main chamber 612. Integrated port dome 620, like integrated port dome 310, may be made from a biocompatible material with self-sealing capabilities, such as silicone.

FIGS. 7A and 7B show three-dimensional views of integrated port assembly 600. In particular, FIG. 7A depicts integrated port assembly installed within an opening 702 in an implant shell 700. As with integrated port assembly 400 and implant shell 500, the edge of opening 702 in implant shell 700 may be angled in a manner complementary to an angle of step 624 of integrated port dome 620, so as to fit snugly against step 624. As show in both FIGS. 7A and 7B, the location of coil 616 is represented within coil housing 614 by dashed lines. Integrated port dome 620 may be attached to an outer surface of implant shell 700, so as to form a seal between integrated port dome and implant shell 700.

The integrated port assemblies disclosed herein, such as integrated port assemblies 400, 600, may serve as, e.g., refill ports in implants which need to be filled and/or refilled, such as tissue expanders. This is described further herein, with respect to FIGS. 10A-10C.

Implants, such as tissue expanders, having integrated port assemblies (e.g., integrated port assemblies 400, 600) may additionally include one or more electronic components for controlling changes to the implants, such as, e.g., inflation or deflation of a tissue expander via an integrated port assembly (e.g., integrated port assembly 400, 600). In some aspects, a tissue expander having an integrated port assembly such as those disclosed herein may further include means to remotely fill/inflate the expander via the integrated port assembly.

In some aspects of the present disclosure, inflation and deflation may be performed automatically according to one or more algorithms or predetermined parameters, and/or may be controlled by user input, such as instructions provided via a user interface of a tablet computer or other electronic device in wireless communication with the sensor package. In at least one example, inflation/deflation may be controlled according to parameters set in a reader and shown in an LED display output of a reader. Readers according to the present disclosure are described in further detail below.

Platform Reader

The present disclosure also includes readers for use with transponders, sensors, and integrated port assemblies disclosed herein. Generally, transponders and integrated port assemblies disclosed herein may be compatible with a variety of commercially available RF readers. Additionally, disclosed herein are readers that may be compatible with multiple types of transponders and coils, which may be able to send and/or receive signals at varying degrees of strength and at varying frequencies. A platform reader is disclosed herein which, in order to detect a given transponder or coil, may broadcast signals in a sweep of frequencies, receive signals in varying degrees of strength in return, and adjust the broadcast signal to correspond to the strongest received signal in order to best pick up return signals from the given transponder or coil.

Figure 8:
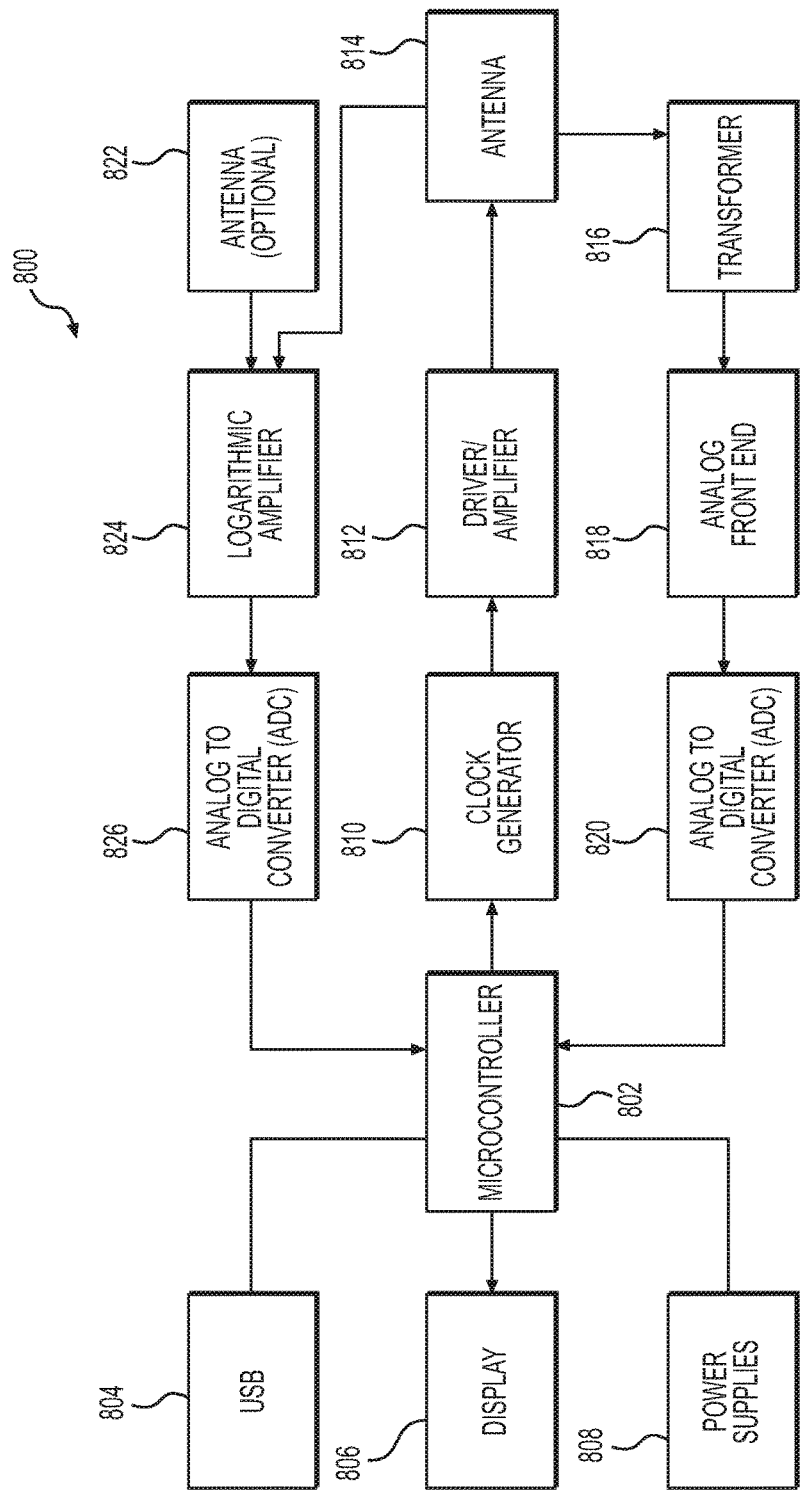
FIG. 8 shows a schematic diagram of a platform reader, in accordance with some aspects of the present disclosure.

FIG. 8 shows a block diagram of components of an exemplary platform reader 800 according to the present disclosure. Platform reader 800 includes a microcontroller 802, which may have one or more USB connections 804 and displays 806. Platform reader 800 also may include one or more power supplies 808 connected to microcontroller 802. Microcontroller 802 may control clock generator 810, which may in turn control a driver/amplifier 812. Driver/amplifier 812 may be connected to an antenna 814. Antenna 814 may be connected to transformer 816, which may in turn be connected to an analog front end 818. An analog to digital converter (ADC) 820 may be connected to analog front end 818 and microcontroller 802.

Antenna 814 may also be connected to a logarithmic amplifier 824. A pickup antenna 822 may also be connected to logarithmic amplifier 824.

Microcontroller 802 may be, for example, a small computer on an integrated circuit, capable of receiving data from a variety of components, and also capable of directing a variety of components to perform their functions. For example, microcontroller 802 may contain one or more computer processing units (CPUs), as well as memory and programmable input/output peripherals. Microcontroller 802 may, for example, receive input and instructions via a digital connection, which may, for example, be a USB connection 804. In alternate embodiments, USB connection 804 may be another type of connection, such as an eSATA connection, a Firewire connection, an Ethernet connection, or a wireless connection. Connection 804 may connect microcontroller 802 to, for example, an input/output device capable of programming microcontroller 802, such as a computer.

Microcontroller 802 may also have a display 806, which may be, for example, an LED display. Display 806 may be configured to display calculations, input, output, and instructions sent and received by microcontroller 802. In some embodiments, display 806 may be configured to display instructions or input received via, e.g., connection 804. In alternate embodiments, display 806 may simply be a series of display lights. In further alternate embodiments, display 806 may be a non-LED display, such as an LCD display or other display.

Platform reader 800 may also include one or more power supplies 808. Power supplies 808 may include any type of power supply compatible with elements of platform reader 800, including, for example, alternating current power supplies, direct current power supplies, battery power supplies, etc. In FIG. 8, power supplies 808 are shown as being connected to microcontroller 802. However, in further embodiments, power supplies may additionally or alternately be connected to any other component of platform reader 800.

Microcontroller 802 may be connected to clock generator 810, which may in turn be connected to driver/amplifier 812. Clock generator 810 may be a circuit that may provide a timed signal having a precise frequency and/or wavelength, through which microcontroller 802 may instruct driver/amplifier 812 to output a sweep of broadcast signals at a desired speed or interval. Driver/amplifier 812 may include, for example, a driver that generates an RF signal, and an electronic amplifier that may generate a low-power RF signal and amplify the signal into a higher power signal. Driver/amplifier 812 may include, for example, any type of RF driver/amplifier known in the art, such as either a solid state or a vacuum tube amplifier.

Driver/amplifier 812 may be connected to antenna 814. Antenna 814 may be, for example, an RF antenna. Antenna 814 may, on the one hand, be connected to transformer 816, which is in turn connected to analog front end 818 and ADC 820. Together, transformer 816, analog front end 818, and ADC 820 may be configured to receive and process signals, e.g., carrier and modulated signals, from antenna 814 and convert them to digital values, for return to microcontroller 802. In particular, transformer 816 may be configured to transform a received high voltage signal from antenna 818 and transform it to a voltage that may be processed by other elements of reader 800 (e.g., analog front end 818, ADC 820, and/or microcontroller 802) without damaging those other elements. Analog front end 818 may be configured to filter out portions of received and transformed signals from transformer 816. For example, analog front end 818 may be configured to process received signals such that carrier signals having the same wavelength and/or frequency as signals broadcasted by antenna 814 are removed, leaving only modulated signals (e.g., signals modulated by a transponder which received and returned a signal from antenna 814). ADC 820 may be configured to convert the filtered modulated signal to a digital value.

Antenna 814 may also be connected to logarithmic amplifier 824, which may also be connected to an optional pickup antenna 822. Pickup antenna 822 may serve as an additional antenna configured to assist in picking up weaker signals. Weak signals received by either antenna 814 or pickup antenna 822 may be amplified by logarithmic amplifier 824 and passed to ADC 826. Logarithmic amplifier 824 may be an amplifier configured to receive weak signals and amplify them on a logarithmic scale, such that they may be processed by ADC 826 and microcontroller 802. ADC 826 may be configured to convert signals received from logarithmic amplifier 824, and provide them to microcontroller 802, which may be configured to assess the strength of signals received from ADC 826. In this manner, platform reader 800 may be able to evaluate and process signals spanning a breadth of signal strength.

In some embodiments of reader 800, microcontroller 802 may be, for example, connected directly to driver/amplifier 812. In such embodiments, microcontroller 802 may be configured to provide a signal frequency and wavelength directly to driver/amplifier 802, without generation of the signal by clock generator 810.

Elements of reader 800 may be permanently or removably connected to one another. For example, antenna 814 and/or pickup antenna 822 may be removably attached to other elements of reader 800.

Figure 9:
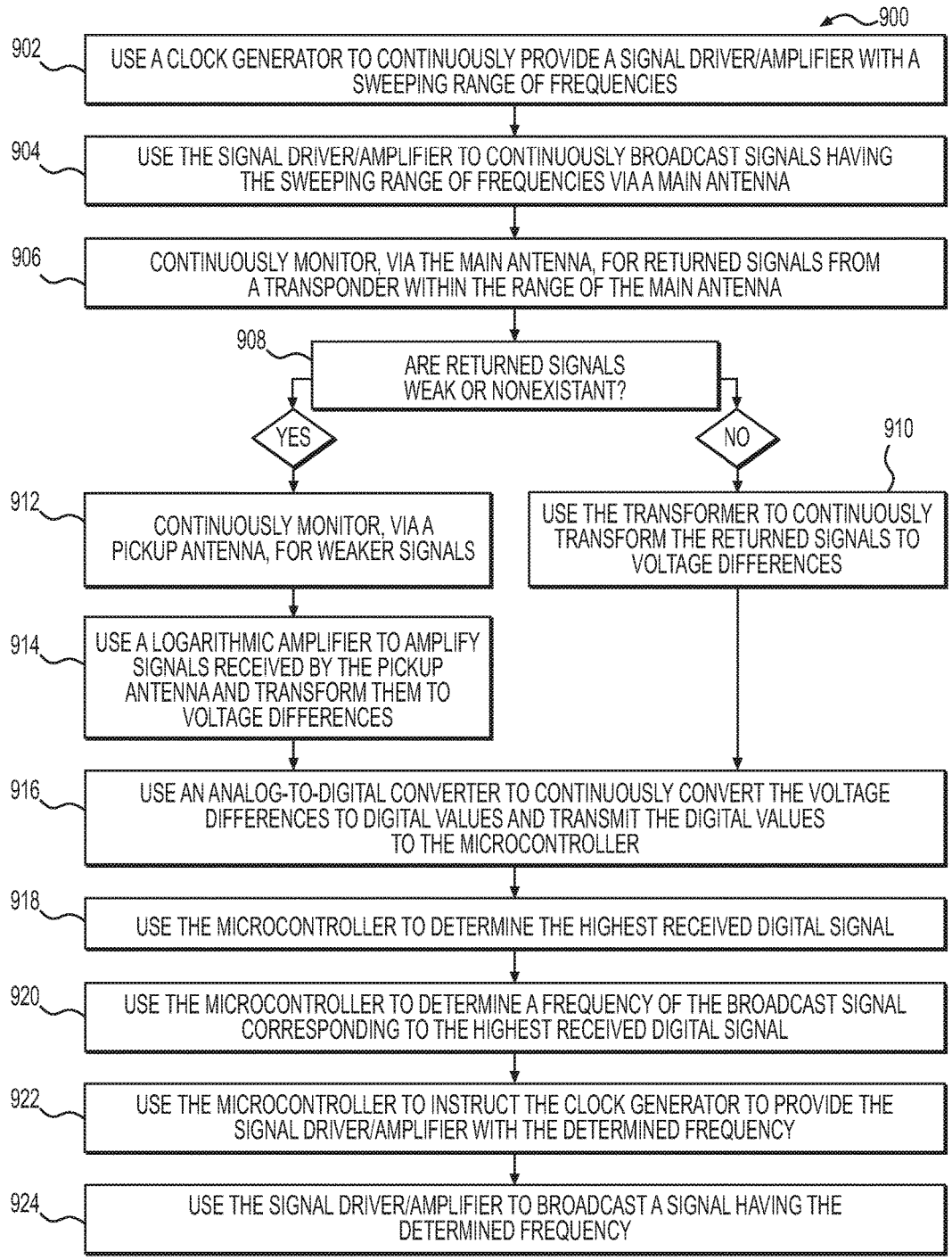
FIG. 9 shows, in block diagram form, steps of an exemplary method of broadcasting a signal, according to further aspects of the present disclosure.

FIG. 9 depicts, in block diagram form, steps of a method 900 for broadcasting a signal having a frequency optimized for a given transponder. Method 900 may be performed using, for example, platform reader 800. According to step 900, a clock generator may be used to continuously provide a signal driver/amplifier with a sweeping range of frequencies. According to step 904, the signal driver/amplifier may be used to continuously broadcast signals having the provided sweeping range of frequencies via a main antenna. According to step 906, returned signals from a transponder within the range of the main antenna may be continuously monitored for via the main antenna. According to step 908, a determination may be made as to whether any returned signals are weak or nonexistent. If not (i.e., if returned signals are strong), then according to step 910 a transformer may be used to continuously transform the returned signals into voltage differences. If so, then according to step 912, a pickup antenna may be used to continuously monitor for weaker signals, and according to step 914, a logarithmic amplifier may be used to amplify signals received by the pickup antenna and transform them into voltage differences. According to step 916, an analog-to-digital converter may be used to continuously convert the voltage differences (transformed in either step 910 or step 914) to digital values and transmit the digital values to the microcontroller. According to step 918, the microcontroller may be used to determine the highest received digital signal. According to step 920, the microcontroller may be used to determine a frequency of the broadcast signal corresponding to the highest received digital signal. According to step 922, the microcontroller may be used to instruct the clock generator to provide the signal driver/amplifier with the determined frequency. According to step 924, the signal driver/amplifier broadcasts a signal having the determined frequency.

According to method 900, a clock generator may be used to continuously provide a signal driver/amplifier with a sweeping range of frequencies. For example, with respect to platform reader 800, microcontroller 802 may provide clock generator 810 with instructions to provide signal driver/amplifier 812 with a sweeping range of frequencies. Frequencies may range from, e.g., about 80 kHz to about 400 kHz. For example, in some embodiments, frequencies may range, e.g., from about 80 kHz to about 300 kHz, from about 100 kHz to about 250 kHz, from about 100 kHz to about 200 kHz, from about 110 kHz to about 150 kHz, from about 110 kHz to about 140 kHz, or from about 120 kHz to about 150 kHz. In some embodiments, a sweeping range of frequencies may include commonly used or standardized frequencies, such as, e.g., about 125 kHz and/or 134.2 kHz. In some embodiments, a sweeping range of frequencies may span 3 or 4 kHz above and below commonly used or standardized frequencies, such as, e.g., a range of from about 121 kHz to about 129 kHz, or from about 130.2 kHz to about 138.2 kHz. In some embodiments, a speed at which the sweeping range of frequencies is provided may depend, for example, on how large the range of frequencies is, and/or how many times a sweep is repeated. In some embodiments, for example, a sweeping range of frequencies may be provided for, e.g., less than a second. In other embodiments, for example, a sweeping range of frequencies may be provided for, e.g., one or more seconds.

According to step 904, the signal driver/amplifier (e.g., driver/amplifier 812) may be used to continuously broadcast signals having the provided sweeping range of frequencies via a main antenna (e.g., antenna 814). The signal driver/amplifier may be instructed to begin continuously broadcasting signals by a controller, such as, e.g., microcontroller 802.

According to step 906, returned signals from a transponder within the range of the main antenna may be continuously monitored for via the main antenna (e.g., antenna 814). The existence and/or strength of returned signals from a transponder within the range of the antenna, such as an RF transponder (e.g., transponder 100, 200), may depend upon, e.g., the frequencies broadcast in step 904 by, e.g., driver amplifier 812. A transponder may be configured to return the strongest signal at a particular frequency, such as, e.g., 125 kHz. Thus, as the signal driver/amplifier approaches that frequency in its sweeping broadcast, the returned signal from the transponder may increase and peak at that frequency.

According to step 908, a determination may be made as to whether any returned signals are weak or nonexistent. Such a determination may be made by, for example, a low signal strength or lack of signals received by microcontroller 802, after any received signals have been processed by transformer 816, analog front end 818, and ADC 820. If not (i.e., if returned signals are strong), then according to step 910 a transformer may be used to continuously transform the returned signals into voltage differences. If so, then according to step 912, a pickup antenna (e.g., pickup antenna 822) may be used in addition to the main antenna (e.g., antenna 814) to monitor for weaker signals, and according to step 914, a logarithmic amplifier (e.g., logarithmic amplifier 824) may be used to amplify weak signals received by either the pickup antenna or the main antenna and transform them into voltage differences that may be converted by an ADC (e.g., ADC 820 or ADC 826).

In an alternative embodiment, a pickup antenna (e.g., pickup antenna 822) may be used in addition to a main antenna to monitor for weaker signals, and a logarithmic amplifier (e.g., logarithmic amplifier 824) may be used to amplify weaker signals received by either the pickup antenna or the main antenna, without first determining whether any returned signals are weak or nonexistent.

According to step 916, an analog-to-digital converter may be used to continuously convert the voltage differences (transformed in either step 910 or step 914) to digital values and transmit the digital values to the microcontroller. For example, ADC 820 may be used to continuously convert voltage differences transformed by transformer 816, and ADC 826 may be used to continuously transform voltage differences amplified by logarithmic amplifier 824. According to step 918, the microcontroller (e.g., microcontroller 802) may be used to determine the highest received digital signal (for example, from the combined pool of digital signals received from both ADC 820 and ADC 826).

According to step 920, the microcontroller may be used to determine a frequency of the broadcast signal corresponding to the highest received digital signal. The highest received digital signal may correspond to an optimal broadcast signal to receive the clearest return from a transponder in the vicinity of one or more antennae (e.g. antenna 814 and pickup antenna 822).

According to step 922, the microcontroller may be used to instruct the clock generator to provide the signal driver/amplifier with the determined frequency, after which, according to step 924, the signal driver/amplifier may be instructed to broadcast a signal having the determined frequency.

The above-disclosed method thereby provides a manner in which a signal frequency may be adjusted to suit a particular transponder. Advantageously, this may allow for a reader, such as platform reader 800, to broadcast a tailored signal to a transponder which may not be configured to respond to an exact standard signal (standard RFID signals include, e.g., 125 kHz and 134 kHz). Because slight differences in, e.g., coil shape, coil size, and number of coil turns may result in a transponder, particularly a relatively small transponder, having an optimal frequency that is slightly different from a standard frequency, and because a relatively small transponder without a ferromagnetic core (such as, e.g., transponders 100, 200) may already have a limited range and signal strength, determining an optimal frequency for a transponder and then reading the transponder at that frequency may result in a stronger, improved return signal than would be received with a standard signal.

Readers, such as platform reader 800, may be used in order to send information to and receive information from transponders disclosed herein, such as, for example, transponders 100, 200, and integrated port assemblies 400, 600. While this disclosure describes platform reader 800 in the context of transponders for use in implants, such as breast implants, it is to be understood that platform reader 800, and methods of using platform reader 800, such as method 900, may be used in other contexts as well.

Figure 10C:
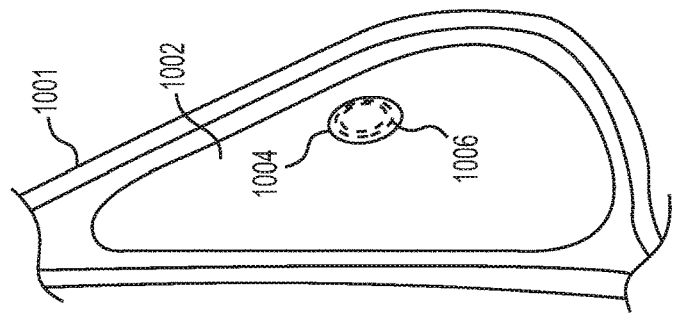
FIGS. 10A-10C show steps in an exemplary method of injecting fluid into an implant, according to some aspects of the present disclosure.
Figure 10B:
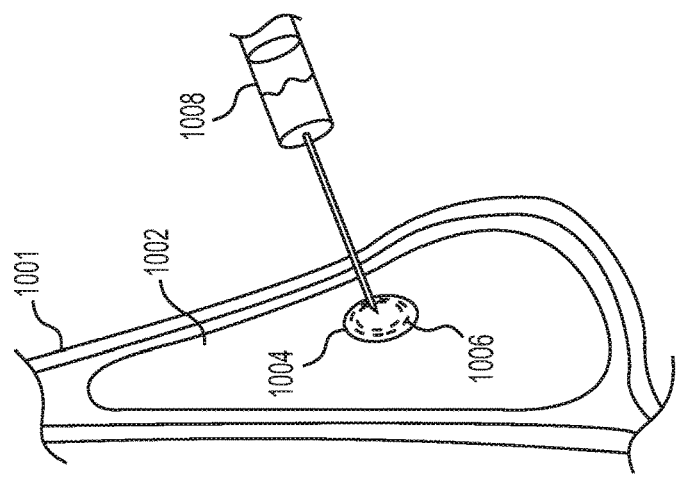
Figure 10A:
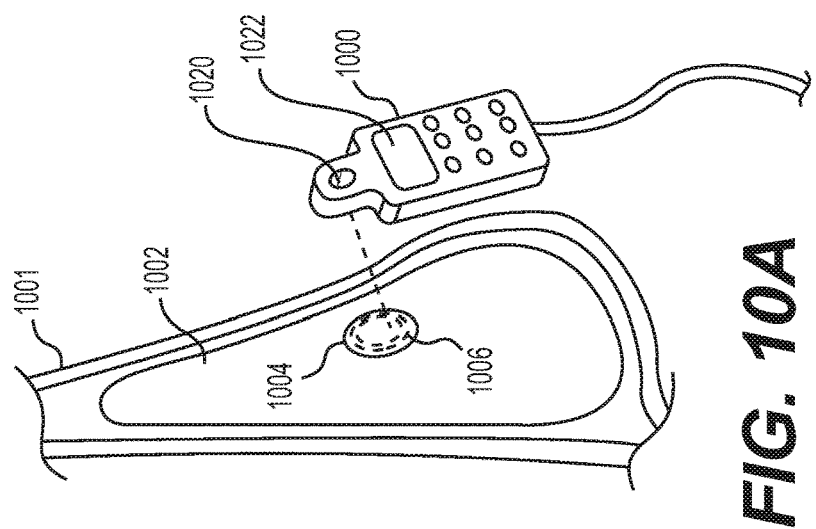

FIGS. 10A-10C depict the use of a reader 1000 to inject fluid into a tissue expander 1002 having an integrated port assembly 1004 equipped with an antenna coil 1006 (shown by dashed lines). As depicted in each figure, a patient may have had a tissue expander 1002 surgically implanted in, adjacent to, or in place of, breast tissue 1001. Reader 1000, for example, may be or share characteristics with platform reader 800. Integrated port assembly 1004 may be or share characteristics with, for example, integrated port assembly 400 or integrated port assembly 600. The center of integrated port assembly 1004 may be identified by an electronic reader looking for the "windowing" or center of the wound antenna coil in each integrated port assembly; e.g., as "a targeting element," as described further below.

As depicted in FIG. 10A, a reader 1000 configured to locate antenna coil 1006 may be used in order to determine the location of antenna coil 1006, and thus integrated port assembly 1004, underneath patient's tissue 1001. Reader 1000 may, for example, have an antenna configured to induce and detect magnetic fields in nearby electromagnetic coils. Reader 1000 may, for example, output a number on a display 1000, indicating a distance between a point on reader 1000 and a center of a core of antenna coil 1006, and may continuously update the output number as reader 1000 is moved over patient tissue 1001. Once reader 1000 displays a number below a given threshold, or otherwise indicates that reader 1000 has located the core of antenna coil 1006, then a physician may prepare to inject fluid at the designated spot in patient tissue 1001.

Once integrated port assembly 1004 has been located, in some embodiments, a mark may be made on the skin of patient tissue 1001 for proper alignment for a fluid injection device with integrated port assembly 1004. In some aspects, reader 1000 may be equipped with a needle guide 1200 to assist with alignment with integrated port assembly 1004. In some aspects of the present disclosure, the needle guide may include a sleeve, which may be sterile and/or disposable so that the reader may be used on multiple patients.

As depicted in FIG. 10B, a fluid injection device 1008 may be used to inject fluid into, and thus expand, tissue expander 1002 through patient's tissue 1001 and integrated port assembly 1004. Fluid injection device 1008 may be, for example, a syringe, such as a manual syringe, an automated syringe, a pipette, or other fluid deposition device. Finally, as depicted in FIG. 10C, once fluid has been injected using fluid injection device 1008, and once fluid injection device 1008 has been withdrawn, tissue expander 1002 may have a larger volume.

Data Analysis and Further Transponder Uses

Multiple combinations of, and uses for, the transponders, sensors, and readers disclosed herein to achieve different results may be possible. Some of these combinations and uses are expanded upon below.

Data Analysis

The present disclosure also includes algorithms that account for characteristics of the physiological environment from which data is being collected. The algorithms may be used to assess and/or analyze the data to provide a translational outcome or output. For example, the algorithms may incorporate particular characteristics and nuances of the materials used in the construction of the medical devices. Such characteristics may include, for example, the chemical composition of the medical devices and/or surface characteristics (or other physical characteristics, such as the dissolution of drugs or agents from the surface or rate of degradation of a biodegradable materials). For example, the particular chemical composition of silicone used in a breast implant or tissue expander and/or the surface properties of the medical devices may affect their interaction with the patient's surrounding tissue. The selection of appropriate materials may be at least partially based on biocompatibility, the ability to reduce or regulate an appropriate immunological response, and/or the ability to be partially or completely inert. Non-permeable materials such as glass may be used to encapsulate sensors and micro-electronics as a suitable type of inert coating. Additionally, or alternatively, the algorithms may include consideration of the depth and location of the medical devices when implanted (e.g., characteristics of the surrounding tissues) and/or potential interference from other active (powered) devices such as other implants.

As a further example, the algorithms may take into account one or more physiological parameters such as, e.g. pH, temperature, oxygen saturation, and other parameters, which may aid in the screening, diagnosis and/or prediction of a disease, disorder, or other health condition (including, for example, tissue inflammation or infection). These algorithms may be designed to filter through data collected from the sensor(s) in order to optimize the 'signal-to-noise ratio', and include formulations that determine the significance of combined analytical data; e.g. pressure, pH and/or temperature in the assessment of infection or tissue inflammation. Other combinations of data may be indicative of foreign (e.g., cancerous) tissues. The algorithms herein may be predictive of structural changes, e.g., by revealing a weakening in a portion of the medical device before failure. For example, the algorithm may identify a weakening in the shell of a breast implant before it ruptures and/or sense a rupture or tear in the shell based on, for example, a change in pressure.

In some aspects, the algorithms may take into account individualized patient data. For example, the algorithms may collectively analyze various data, both data collected from the sensor(s) integrated into a medical device implanted into a patient and data specific to that individual patient. For example, a sensor that collects pH, pressure, and temperature may provide clinical data more meaningful in some respects if the algorithm contemplates other physiological data (such as, e.g., blood parameters, genomics, tissue elasticity, and/or other health parameters).

Data analysis according to the present disclosure may include anti-collision technologies for low frequency systems, e.g., having the ability to read data from multiple sensors at the same time. Transponders that comprise an RF antenna generally have the ability to transmit and receive data. Communication of data may include specific ASIC programming, which may depend on the frequency of RF signals. Therefore, each transponder may selectively communicate with one or more other sensors in sufficient proximity, which may include transponders implanted elsewhere in the patient.

Medical Device Information

Device Breach/Failure: pH Change

According to some aspects of the present disclosure, the transponders disclosed herein may provide information on the status of the implanted medical device, when used in combination with various types of sensors. For example, pH sensors may be used to detect a breach of interstitial fluid such as blood and/or proteins that may infiltrate a failing medical implant. Such pH sensors may be positioned at various locations around the surface of the medical device. For example, one or more pH sensors may be coupled to, or embedded in, the surface of a breast implant or tissue expander. Multiple sensors, coupled with transponders, may be in communication with one another via frequency linking, e.g., ad hoc or hard wired. A change in pH may be detected by the sensor(s) in case of a breach of the medical device. For a breast implant, for example, a change in pH may result from a breach in the outer shell wall, or a breach in a portion of the shell with permeable access to the sounding tissue. Some medical devices according to the present disclosure may include a conduit that allows passive flow (e.g., convection or conduction) of external interstitial fluid to the sensor residing deeper inside the medical device, such that a bodily fluid such as blood may diffuse into the medical device due to a breach and be detected by the sensor.

Device Failure: Other Detection Methods

According to some aspects of the present disclosure, an implantable medical device may include a meshed nanoscale detection system using fluid chemistry, chemical, electronic or mechanical substrate materials to detect a breach in the implantable medical device, such as a shell breach. Additionally, or alternatively, the medical device may include external and/or internal systems using infrared (IR) or low wave light (or low wave electronic field) for examining breach detection with chip enhancers within the medical device. This type of system may help detect a disruption in a continuum, such as a break in a wavelength or electromagnetic field from an interference caused by a mechanical rupture in the medical device. In this type of system, for example, a chip enhancer may use the full duplex system of coupling to look for a particular antenna's highest (strongest) resonant frequency (highest Q) and adjust to read data at that level. The search for the highest Q may be performed with specialized crystals within a range and a kernel placed in the firmware of a reader (e.g., reader 800).

As an example, an implantable medical device may include an intact electroconductive barrier as one shell component of the implantable medical device, such that breach of a shell of the implantable medical device, including the electroconductive barrier, may cause a change in electrical resistance of the electroconductive barrier. The implantable medical device may further include a transponder (e.g., transponders 100, 200) within a space enclosed by the electroconductive barrier (e.g., within the implant). Such a transponder may be, for example, an RF transponder, as has been previously disclosed herein. In some embodiments, such a transponder may be configured to receive power via induction by, e.g., an external reader, as has been previously described herein. In further embodiments, such a transponder may be provided with an independent power source, such as a battery. A breach in the electroconductive barrier may cause a change in the ability of an external reader (e.g., reader 800) to send transmissions to and/or receive transmissions from the transponder within the space enclosed by the electroconductive barrier. Thus, the presence of, and changes in, the electroconductive barrier may assist in determining whether a part of an implantable medical device (e.g., a shell) is intact, or has been breached or otherwise damaged.

FIG. 11 depicts an example of a portion of an implant shell which may contain an electroconductive barrier layer. An implant having a multilayered shell 1100 may be modified to include an electroconductive layer 1106 in between an inner layer 1104 of shell 1100 and an outer layer 1102 of shell 1100. Electroconductive layer 1106 may be configured to resist, block, reduce, interfere with, or impede transmission of signals, such as RF signals, across the shell 1100 of the implantable medical device, as long as the electroconductive layer remains intact.

Inner layer 1104 and outer layer 1106 of shell 1100 may be made of any suitable biocompatible material. In some embodiments, inner layer 1104 and outer layer 1106 may be made of non-electroconductive materials. For example, one or more of inner layer 1104 and outer layer 1106 may be made of silicone, or plastic, such as PEEK.

Electroconductive layer 1106 may be made of any biocompatible material that blocks, reduces, interferes with, or impedes transmission of RF signals across the layer. For example, in some embodiments, electroconductive layer 1106 may be a layer of carbon. Electroconductive layer 1106 may be, for example, a solid layer, or may be a layer having a regular or irregular mesh pattern (e.g., resembling a cage or a net). In embodiments where the electroconductive layer 1106 has a mesh pattern, any gaps in the mesh pattern may be sufficiently small to prevent signals from being received by or transmitted from a transponder enclosed by electroconductive layer 1106. In some embodiments, electroconductive layer 1106 may be, or may be similar to, a Faraday cage or enclosure.

In some embodiments, electroconductive layer 1106 may be, for example, between inner layer 1104 and outer layer 1102 of implant shell 1100. In further embodiments, electroconductive layer 1106 may be, for example, an innermost layer of an implant shell 1100. In yet further embodiments, electroconductive layer 1106 may be, for example, an outermost layer of an implant shell 1100. In some embodiments, implant shell 1100 may have multiple inner layers 1104, multiple outer layers 1102, and/or multiple electroconductive layers 1106.

Integrity of electroconducitve layer 1106 (and thus, of a component of the implantable medical device, such as a shell component) may be tested, for example, by an external reader, such as reader 800, which may be configured to send transmissions to, and/or receive transmissions from, a transponder enclosed by electroconductive layer 1106 (e.g. transponders 100, 200). As has been previously described herein, the reader (e.g., reader 800) may be configured to determine and broadcast a signal at a frequency calibrated specifically for the transponder. If electroconductive layer 1106 is intact (e.g., if it has not been breached, damaged, or subject to manufacturing defect), then the reader may receive no signal, or a faint or low signal, from the transponder enclosed by electroconductive layer 1106. If electroconductive layer 1106 is not intact, then the reader may receive a stronger signal from the transponder enclosed within electroconductive layer 1106, due to the barrier function of electroconductive layer 1106 being disrupted. Thus, electroconductive layer 1106 may assist in determining whether an implantable medical device is defective.

In some examples, electroconductive layer 1106 may have a color, such that it may be visually inspected for defects, imperfections, or breaches. The color may, in some embodiments, render electroconductive layer 1106 opaque or semi-opaque. For example, electroconductive layer 1106 may be black, or may be blue, green, pink, red, white, or any other color.

In further examples, a reader may provide an ASIC with power to probe the barrier for a change using an electromagnetic sensor. Similar techniques may be used with electrically conductive nanocomponents or nanomaterial. For example, electrically conductive nanomaterials may be sprinkled within individual mono layers of a shell (e.g., providing a wire like substrate), which, if broken or disrupted, may cause a change in resistance. In yet another example, a small low energy light source may be placed within the medical device, and when powered, the light may shine and reflect off a material coating the inner layer of the shell. But if breached or broken, the light may not reflect, providing for a change detected by the reader and calculated against the parameters of the initial calibration.

Advantageously, such electroconductive layers and reflective coating layers may be used to determine whether an implantable medical device has been breached, broken, or has a manufacturing defect both before and after implantation. In particular, such layers may assist in noninvasively determining whether an implantable medical device (e.g., a breast implant) is or has become defective. In some embodiments, a reader as disclosed herein (e.g., reader 800) may be used, in conjunction with an implant having a layer such as the layers described above, by, e.g., a doctor, a nurse, a patient, or another individual associated with either the implantable medical device or the patient to determine whether the implantable medical device is or has become defective. Thus, advantageously, such layers may also assist in allowing for noninvasive examining/analysis of, e.g., structural integrity of an implantable medical device by a variety of individuals.

Device Position/Orientation

In addition to information about the failure of a medical device, the transponders disclosed herein (e.g., transponders 100, 200) may be used to determine whether the medical device maintains its appropriate implanted position and orientation. After implantation, for example, a medical device may migrate over time from its proper position. Sensors, coupled with transponders according to the present disclosure, may measure and project data indicative of cyclo-rotation, vibrational, torsional or misalignment (e.g., movement) of an implanted medical device. Such sensors may capture the number of cycles an articulating surface may be exposed to (i.e. a knee or hip implant, annulus of a heart valve, or frequency of changes in pressure gradients in a shunt or vascular graft). The sensors may include elements such as a gyro, a type of accelerometer, which may measure changes in angulation and/or angular velocity. Other suitable sensors include fiber-optic rotational sensors, which may comprise an active light source and reader. An inertial measurement unit (IMU) may be used to combine information from two or more sensors, such as gyros, 3-D accelerometers, magnetometers, and/or GPS units to determine information such as device orientation and velocity vector. In some aspects, a combination of sensors may be used to determine comprehensive status information on a medical device.

In some aspects, the sensor(s), coupled with transponders of the present disclosure, may measure the change of orientation of radiopaque markers in relationship to one or more anatomical features or landmarks. For example, a patient may undergo periodic X-rays to assess location and orientation information. In such cases, a sensor configured for dosimetry measurements may be used.

Data Transmission

Data about an implantable medical device may be transmitted and received constantly, periodically, on demand (in response to user inquiry), or when certain values or parameters are detected. In some examples, a transponder may include a dual-processor ASIC approach, wherein a specific ASIC may be used for medical management of a transponder (e.g., to determine when the sensor actively "reads" or "sleeps"), and the other ASIC may be used for power management (e.g., to regulate how much energy is provided to the system). The power management ASIC may include an algorithm to maintain an appropriate level of charge, e.g., avoid complete discharge.

The method and/or frequency of data transmission may depend on the relevance of the data to the patient or given medical context. For example, for more serious conditions or events such as a device rupture, a transponder coupled with a particular sensor or sensors configured to detect rupture may also be configured to push the data to an external device, such a mobile device or other electronic device. This type of data transmission may be incorporated into an algorithm and used as part of an active system. Further, for example, data indicative of tissue inflammation or inappropriate rotation/placement of the medical device may be transmitted on demand by sending a wireless signal from the external device periodically (e.g., on a weekly, biweekly, or monthly basis). On-demand transmission of data may be initiated, for example, when the patient is reminded from an uploaded app on a mobile device. A transponder configured for constant or nearly constant transmission of data may include a power source or recharging element sufficient to maintain power over an extended period of time.

Lab-On-a-Chip

The transponders disclosed herein, combined with sensors disclosed herein, may be configured as a lab-on-a-chip, e.g., a subset of microelectromechanical systems (MEMS) that may employ microfluidics to capture and identify and/or quantify biomarkers, e.g., for proteomics. Such micro analytic systems may use Surface Plasmon Resonance (SPR) and related systems and techniques to detect a wide variety of biomolecular interactions that otherwise may have low spectroscopic signals or reaction heats. These systems may provide data analytics to optimize therapeutic devices and treatments related to binding affinities of antibodies, drug/cellular membrane absorption rates, and/or tissue sensitivity levels that may impact the dosage (dosimetry) of chemotherapy or radiation therapies. Such lab-on-a-chip sensor and transponder combinations may comprise a suitable power source. These types of sensor and transponder combinations may be useful as an assessment tool, e.g., to determine if a particular patient would respond better to adjunctive substrates such as hyaluronic acid or chitosan.

Data Output

The present disclosure further includes means to optimize the data output for readers, including the range and sophistication to decode specific algorithms. Data may be encoded for patient confidentiality, in compliance with HIPPA regulations. Data may be accessible by a mobile device such as a smartphone or tablet computer, e.g., via password- or fingerprint-protected access.

The transponders disclosed herein may communicate on specific radiofrequencies, e.g., to optimize the inductive recharging of an active sensor. For example, the RF antenna may function as a receiver for inductive energy to recharge embedded power cells. Such range of frequencies may be utilized so that the sensors do not interfere with other communication frequencies or cause heating of components or coatings of the sensors or heating of surrounding patient tissues. Exemplary ranges include, for example, from about 80 kHz to about 400 kHz, such as from about 80 kHz to about 350 kHz, from about 80 kHz to about 320 kHz, from about 100 kHz to about 300 kHz, from about 100 kHz to about 250 kHz, from about 100 kHz to about 200 kHz, from about 100 kHz to about 180 kHz, from about 100 kHz to about 150 kHz, from about 100 kHz to about 140 kHz, from about 110 kHz to about 140 kHz, from about 120 kHz to about 140 kHz, or from about 125 kHz to about 135 kHz. Reference may be made to ISO standards 11784/85.

The transponders disclosed herein may include one or more ASICs that provide for storage and appropriate power management that utilizes a threshold of self-containment so that the system does not completely discharge, which may lead to explantation. A self-contained system is generally configured to regulate itself, and prevent a total discharge. For example, the ASICs herein may place the power source in hibernation once the power level reaches a given threshold, therefore allowing for recharging rather than becoming a totally "dead" battery.

Security

The transponders, readers, implants, and port assemblies disclosed herein may be incorporated into a security system for, e.g., cloud data access. Such a security system may provide for push opportunities (alerts) to user devices, such as, e.g., the readers disclosed herein, or other secured personal devices such as tablets, computers, smartphones, mobile devices, etc. Such a security system may thereby provide for tracking of transponders, implants, and implant parts from manufacturer to surgeon; and possibly from surgeon to patient. Devices used to receive and transmit information between the medical device, computer/mobile device, and cloud/Internet server may include, but are not limited to, an RF reader with WIFI connectivity, and Bluetooth connectivity to an electronic device connected to the Internet. According to some aspects, manufacturers, physicians, and/or patients may interact with such a security system through an RF reader and/or an app on a mobile electronic device.

While the figures and disclosure herein depict several exemplary configurations of transponders, sensors, assemblies, readers, implants, and several exemplary methods of use thereof, one of ordinary skill in the art will understand that many other configurations and variations on methods are possible and may be appropriate for a given implant, patient, procedure, or application, based on implant size, shape, orientation and intended location in the patient body. The examples of devices, systems, and methods herein are intended to be exemplary and are not comprehensive; one of ordinary skill in the art will also understand that some variations on the disclosed devices, systems, and methods herein are also contemplated within this disclosure.

We claim:

1. A transponder, comprising:
   a coil comprised of a wire, wherein
   a length of the transponder measures between about 5 mm and about 30 mm;
   a width of the transponder measures between about 2 mm and about 5 mm and is less than the length of the transponder;
   the transponder does not include a ferromagnetic material; and
   the wire is wound along the length of the transponder.

2. The transponder of claim 1, further comprising an integrated circuit chip coupled to the coil.

3. The transponder of claim 2, further comprising a capsule enclosing the coil and the integrated circuit chip coupled to the coil.

4. The transponder of claim 1, wherein a diameter of the coil is smaller than the length of the transponder and greater than the width of the transponder.

5. The transponder of claim 1, wherein the transponder is configured to send and/or receive information within a range of from about 1 inch to about 5 feet.

6. The transponder of claim 1, wherein the wire is an enameled copper wire.

7. The transponder of claim 6, wherein the wire is wound around a core comprising biocompatible poly-ether-ether-ketone (PEEK).

8. The transponder of claim 1, wherein the transponder is cylindrical.

* * * * *